US009669151B2

(12) United States Patent
Rae et al.

(10) Patent No.: US 9,669,151 B2
(45) Date of Patent: Jun. 6, 2017

(54) THERAPEUTIC COMPOSITIONS FOR VIRAL-ASSOCIATED DISEASE STATES AND METHODS OF MAKING AND USING SAME

(71) Applicant: ImMutriX Therapeutics, Inc., Rapid City, SD (US)

(72) Inventors: Carol A. Rae, Rapid City, SD (US); Jan Simoni, Rapid City, SD (US); Grace Simoni, Rapid City, SD (US); John F. Moeller, Rapid City, SD (US)

(73) Assignee: IMMUTRIX THERAPEUTICS, INC., Rapid City, SD (US)

( * ) Notice: Subject to any disclaimer, the term of this patent is extended or adjusted under 35 U.S.C. 154(b) by 0 days.

(21) Appl. No.: 14/642,538

(22) Filed: Mar. 9, 2015

(65) Prior Publication Data

US 2015/0297821 A1 Oct. 22, 2015

Related U.S. Application Data

(60) Provisional application No. 61/981,061, filed on Apr. 17, 2014, provisional application No. 62/055,392, filed on Sep. 25, 2014.

(51) Int. Cl.
  *A61M 1/36* (2006.01)

(52) U.S. Cl.
  CPC ..... *A61M 1/3679* (2013.01); *A61M 2202/206* (2013.01)

(58) Field of Classification Search
  CPC ..... A61M 1/34; A61M 1/3486; A61M 1/3496
  USPC ............................................ 435/2; 604/5.04
  See application file for complete search history.

(56) References Cited

U.S. PATENT DOCUMENTS

| | | | |
|---|---|---|---|
| 3,269,911 A * | 8/1966 | Gibbon, Jr. et al. | 424/529 |
| 3,888,250 A * | 6/1975 | Hill | 604/6.06 |
| 3,959,128 A * | 5/1976 | Harris | A61M 1/3679 |
| | | | 128/DIG. 3 |

(Continued)

FOREIGN PATENT DOCUMENTS

WO 2011070363 A1 6/2011

OTHER PUBLICATIONS

Global Alert and Response (GAR), "Ebola Virus Disease," World Health Organization, http://www.who.int/csr/don/archive/disease/ebola/en/, downloaded from Internet on Dec. 16, 2014, 10 pages.

(Continued)

*Primary Examiner* — Dirk Bass
(74) *Attorney, Agent, or Firm* — Wick Phillips Gould & Martin LLP; Jerry C. Harris, Jr.

(57) ABSTRACT

A method comprising obtaining a bodily fluid from a subject; contacting the bodily fluid with an adsorbent material comprising a synthetic carbon particle (SCP) to produce a first filtrate having a level of disease mediators (y); contacting the first filtrate with an adsorbent material comprising the SCP and an anion exchange resin where the ratio of SCP to anion exchange resin is from about 0.1:100 to 100:0.1 to produce a second filtrate; contacting the second filtrate with an adsorbent material comprising the SCP and a cation exchange resin where the ratio of SCP to cation exchange resin is from about 1:100 to produce a third filtrate; and administering the third filtrate to the subject.

16 Claims, 12 Drawing Sheets

(56) References Cited

U.S. PATENT DOCUMENTS

| | | | | |
|---|---|---|---|---|
| 5,726,118 | A | * | 3/1998 | Ivey .................... B01J 21/18 502/180 |
| 5,763,430 | A | | 6/1998 | Zasloff |
| 5,876,756 | A | * | 3/1999 | Takada et al. ............. 424/489 |
| 7,951,789 | B2 | | 5/2011 | Sommadossi et al. |
| 8,796,423 | B2 | | 8/2014 | Li et al. |
| 2001/0018179 | A1 | * | 8/2001 | Hei ........................ A61L 2/00 435/2 |
| 2004/0228829 | A1 | * | 11/2004 | Roberts et al. ............. 424/78.1 |
| 2012/0251502 | A1 | | 10/2012 | Towner et al. |
| 2013/0072845 | A1 | | 3/2013 | Tennison et al. |

OTHER PUBLICATIONS

"WHO Recommends Using Ebola Survivors' Blood to Treat Others," ScienceDaily, http://www.sciencedaily.com/videos/cb880ac8092bb9004fa3a761162db952.htm, Sep. 6, 2014, 3 pages.
"Magnetic device could cure bad blood," http://www.3news.co.nz/world/magnetic-device-could-cure-bad-blood-2014091506#axzz3RZDn0Kpz, 3 News, Sep. 15, 2014, 2 pages.
"Ebola kills Liberia doctor despite ZMapp treatment," http://www.bbc.com/news/world-africa-28925491, BBC News Africa, Aug. 25, 2014, 3 pages.
Bray, Mike, et al., "Ebola virus: The role of macrophages and dendritic cells in the pathogenesis of Ebola hemorrhagic fever," The International Journal of Biochemistry & Cell Biology, 2005, pp. 1560-1566, vol. 37, Elsevier Ltd.
Cohen, Elizabeth, "Ebola in the air? A nightmare that could happen," CNN Health, http://www.cnn.com/2014/09/12/health/ebola-airborne/, Oct. 6, 2014, 5 pages.
Hensley, Lisa E., et al., "Proinflammatory response during Ebola virus infection of primate models: possible involvement of the tumor necrosis factor receptor superfamily," Immunology Letters, 2002, pp. 169-179, vol. 80, Elsevier Science B.V.
House, Thomas, "Epidemiological dynamics of Ebola outbreaks," Epidemiology and global health | Microbiology and infectious disease, 2014, pp. 1-8, eLIFE, House.
Howell, Carol A., et al., "The in vitro adsorption of cytokines by polymer-pyrolysed carbon," Biomaterials, 2006, pp. 5286-5291, vol. 27, Elsevier Ltd.
Ji, Xin, et al., "Mannose-binding lectin binds to Ebola and Marburg envelope glycoproteins, resulting in blocking of virus interaction with DC-SIGN and complement-mediated virus neutralization," Journal of General Virology, 2005, pp. 2535-2542, vol. 86.
Leroy, E. M., et al., "Human asymptomatic Ebola infection and strong inflammatory response," Early Report, Jun. 24, 2000, pp. 2210-2215, vol. 355, The Lancet.
McDonald, Donald M., "Endothelial Gaps: Plasma Leakage During Inflammation," Trendsetters: News in Pyschological Sciences, Apr. 1998, pp. 104-105, vol. 13, Int. Union Physiol. Sci./Am.Physiol. Soc.
McElroy, Anita K., et al., "Biomarker Correlates of Survival in Pediatric Patients with Ebola Virus Disease," Emerging Infectious Diseases, www.cdc.gov/eid, Oct. 2014, pp. 1683-1690, vol. 20, No. 10.
Okumura, Atsushi, et al., "Interaction between Ebola Virus Glycoprotein and Host Toll-Like Receptor 4 Leads to Induction of Proinflammatory Cytokines and SOCS1," Journal of Virology, Jan. 2010, pp. 27-33, vol. 84, No. 1, American Society for Microbiology.
Qiu, Xiangguo, et al., "Reversion of advanced Ebola virus disease in nonhuman primates with ZMapp," Nature, Oct. 2, 2014, pp. 47-53 plus 8 pages of additional information, vol. 514, Macmillan Publishers Limited.
Sanchez, Anthony, et al., "Filoviridae: Marburg and Ebola Viruses," Fields Virology, 5th Edition, Chapter 40, 2007, 93 pages, Lippincott Williams & Wilkins.
Sullivan, Nancy, et al., "Ebola Virus Pathogenesis: Implications for Vaccines and Therapies," Journal of Virology, Sep. 2003, pp. 9733-9737, vol. 77, No. 18.
Szabo, Liz, "CDC: Ebola could infect 1.4 million people by January," USA Today, http://www.usatoday.com/story/news/nation/2014/09/22/ebola-last-forever/16072019/, Sep. 23, 2014, 4 pages.
Takada, Ayato, et al., "The pathogenesis of Ebola hemorrhagic fever," TRENDS in Microbiology, Oct. 2001, pp. 506-511, vol. 9, No. 10, Elsevier Science Ltd.
Filing receipt and specification for provisional patent application entitled "Therapeutic Compositions for Viral-Associated Disease States and Methods of Making and Using Same," by Carol A. Rae, filed Sep. 25, 2014 as U.S. Appl. No. 62/055,392.
Filing receipt and specification for provisional patent application entitled "Plasma Detoxification," by Craig P. Roberts, et al., filed Apr. 17, 2014 as U.S. Appl. No. 61/981,061.
Filing receipt and specification for provisional patent application entitled "Plasma Detoxification," by Craig P. Roberts, et al., filed Apr. 5, 2013 as U.S. Appl. No. 61/809,107.

* cited by examiner

US 9,669,151 B2

THERAPEUTIC COMPOSITIONS FOR VIRAL-ASSOCIATED DISEASE STATES AND METHODS OF MAKING AND USING SAME

CROSS-REFERENCE TO RELATED APPLICATIONS

The present application is a non-provisional of and claims priority to U.S. Provisional Application No. 61/981,061, filed on Apr. 17, 2014 and entitled "Plasma Detoxification." and U.S. Provisional Application No. 62/055,392, filed on Sep. 25, 2014 and entitled "Therapeutic Compositions for Viral Associated Disease States and Methods of Making and Using Same," each of which is incorporated by reference herein in its entirety.

TECHNICAL FIELD

Generally disclosed herein are compositions, systems, and methods for the treatment of subjects experiencing a viral-associated disease state. More specifically disclosed herein are methodologies for the treatment of subjects suffering from immune suppression as the result of a viral infection.

BACKGROUND

Suppression of the immune system is a common symptom observed in individuals infected with viruses such as the Ebola virus, Lassa virus, and Marburg virus. Ebola virus, Lassa Virus, and Marburg virus belong to a taxonomically diverse set of single-stranded ribonucleic acid (ssRNA) viruses from four diverse viral families Arenaviridae, Bunyaviridae, Filoviridae, and Flaviviridae. These viruses cause an acute systemic febrile syndrome called viral hemorrhagic fever (VHF). Other examples of viruses that cause immune system suppression include the Hantaviruses which are single-stranded, enveloped, negative sense RNA viruses in the Bunyaviridae family; MERS-coronavirus (MERS-CoV) which is a betacornavirus derived from bat; Influenza A virus subtype H5N1, also known as A(H5N1) or simply H5N1, which is a subtype of the influenza A virus that can cause illness in humans and many other animal species; and Influenza A (H1N1) virus which is an othomyxovirus and a subtype of influenza A virus that was the most common cause of human influenza (flu) in 2009.

A need exits for additional methods of effectively treating subjects suffering from infection with these viruses. For example, a recent severe outbreak of VHF on the African continent has captured global attention. The World Health Organization (WHO) cites the first cases of the largest and most complex Ebola outbreak to date were noted in March 2014. The gravity of the situation surrounding the recent Ebola outbreak reflects an urgent need for effective, inexpensive, and robust compositions and methodologies for the treatment of subjects suffering from viruses such as Ebola, Hanta, MERS, and influenza.

SUMMARY

Disclosed herein is a method comprising obtaining a bodily fluid from a subject having a level of disease mediators (y); contacting the bodily fluid with an adsorbent material comprising a synthetic carbon particle (SCP) to produce a first filtrate; contacting the first filtrate with an adsorbent material comprising the SCP and an anion exchange resin where the weight ratio of SCP to anion exchange resin is from about 0.1:100 to 100:0.1 produce a second filtrate; contacting the second filtrate with an adsorbent material comprising the SCP and a cation exchange resin where the weight ratio of SCP to cation exchange resin is from about 0.1:100 to 100:0.1 produce a third filtrate; and administering the third filtrate to the subject.

Also disclosed herein is an extracorporeal system comprising at least three adsorbent materials, an access disconnection detector, and a computer system.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
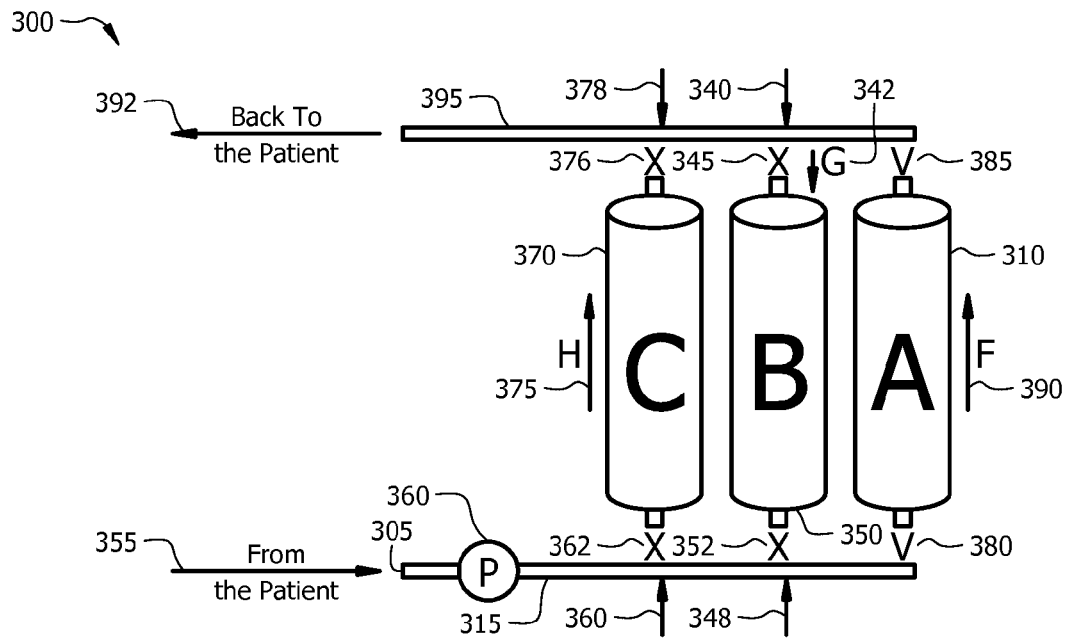
FIGS. 1 and 2 depict embodiments of an apparatus disclosed herein.

Disclosed herein are methodologies and compositions useful for the treatment of subjects suffering from a viral-associated disease state that can result in immunosuppression, such as for example infection with the Ebola virus, Marburg virus, and Hanta virus. Hereinafter, such viruses which cause an infection that can result in immunosuppressive events in the infected subject are collectively termed viruses-associated with immunosuppressive events (VISE). Also disclosed herein are apparatuses useful in the treatment of subjects suffering from a VISE. In an embodiment, the compositions disclosed herein comprise adsorbent materials that are utilized in conjunction with one or more apparatuses of the type disclosed herein in the treatment of subject suffering from a VISE. Herein the term adsorbent material is used for simplicity and it is to be understood the term "adsorbent" does not necessarily refer to the mechanism of action of the material.

The term "subject," as used herein, comprises any and all organisms and includes the term "patient." A subject to be treated according to the methods described herein may be one who has been diagnosed by a medical practitioner as being infected with a VISE. Diagnosis may be performed by any suitable means. A subject in whom the development of an infection is being prevented may or may not have received such a diagnosis. One skilled in the art will understand that a subject to be treated according to the present disclosure may have been subjected to standard tests to diagnose an infection with a VISE or may have been identified, without examination, as one at high risk for infection with a VISE due to the presence of one or more risk factors (e.g., proximity to or contact with the bodily fluids of a subject known to be infected with VISE etc.).

Herein "treating" refers to utilizing the disclosed methodologies and compositions for prophylactic and/or therapeutic purposes. Prophylactic treatment may be administered, for example, to a subject who is not yet ill, but who is susceptible to, or otherwise at risk of a particular disorder, e.g., VISE. Therapeutic treatment may be administered, for example, to a subject already suffering from a disorder in order to improve or stabilize the subject's condition (e.g., a patient already suffering from a VISE). Thus, in the claims and embodiments described herein, treating refers to a subject undergoing, either for therapeutic or prophylactic purposes, the methodologies disclosed herein.

In some instances, as compared with an equivalent untreated control, treatment may ameliorate a disorder or a symptom thereof. As used herein, amelioration of the disorder or symptoms thereof by undergoing the methodologies disclosed herein refers to any lessening, whether lasting or transient, which can be attributed to or associated with undergoing the methodologies disclosed herein. In some instances, treating can result in the inhibition of viral infection, the treatment of the infection, and/or the amelioration of symptoms of the infection. Confirmation of treatment can be assessed by detecting an improvement in or the absence of symptoms, or by the inability to detect the presence of the infectious agent and/or disease mediators in the treated subject.

In an embodiment, a method of the present disclosure comprises (i) contacting the bodily fluid of a subject with an apparatus for removal of one or more components present in the bodily fluid to produce a decontaminated bodily fluid; and returning at least a portion of the decontaminated bodily fluid to a subject. As used herein the term "bodily fluid," includes inter alia plasma, whole blood, and cerebrospinal fluid. In an embodiment, at least a portion of the bodily fluid is removed from the test subject. In an embodiment, the bodily fluid comprises whole blood or plasma.

In an alternative embodiment, a method of the present disclosure comprises contacting at least a portion of a subject's blood with an apparatus for removal of one or more materials present in the blood to produce decontaminated blood; and returning at least a portion of the decontaminated blood to the subject.

In an alternative embodiment, a method of the present disclosure comprises contacting at least a portion of the blood of a subject suffering from a VISE with an apparatus of the type disclosed herein. The method may further comprise recovering at least a portion of the subject's blood to obtain a decontaminated blood. The method may further comprise administering at least a portion of the decontaminated blood to the subject.

In an alternative embodiment, a method of the present disclosure comprises identifying a subject suffering from or at risk for the development of a VISE. The method may further comprise performing extracorporeal cleansing of at least a portion of the subject's blood utilizing the apparatuses and compositions disclosed herein to generate a decontaminated blood. The method may further comprise administering at least a portion of the decontaminated blood to the subject.

In an embodiment, a method comprises obtaining a blood sample from a subject diagnosed with and/or at risk for development of a VISE. The methodologies disclosed herein may be utilized in the treatment of subjects infected with viruses from viral families such as Arenaviridae, Bunyaviridae, Filoviridae, Flaviviridae, Coronavirinae, Bunyaviridae, and Orthomyxoviridae. For example, the subject may be infected with a VISE such as the Hantavirus, MERS-coronavirus (MERS-CoV), Influenza A virus subtype H5N1, Influenza A (H1N1) virus, Ebola Virus, Marburg virus, Lassa virus, or combinations thereof.

Hereinafter for simplicity, the disclosure may refer specifically to the treatment of Ebola infected subjects, although it is to be understood the subject matter disclosed herein may be utilized in the treatment of VISEs from other viral sources such as those disclosed herein. Diagnosis of and/or assessment of the risk for development of a VISE may be made by a healthcare professional using any suitable methodology. As known to the ordinarily skilled artisan, the clinical features of a VISE vary according to the source of the virus.

In an embodiment, a blood sample is obtained from a subject who is in fluid communication with an extracorporeal apparatus. The subject may be infected with a VISE or may be suspected of being infected with a VISE. An embodiment of an apparatus suitable for use in the present disclosure is depicted in FIG. 1. In an embodiment, the apparatus 300 comprises an inlet 305 in fluid communication with a pump 360 which regulates access and fluid communication with conduit 315. The apparatus 300 may be connected to a subject through establishing a means of blood flow from the subject to inlet 305. An arterial access of the subject 355 may be used to establish a means of blood flow from the subject to the inlet 305. As a safety measure, apparatus 300 in one embodiment includes a plurality of electrodes (not shown), such as two to four electrodes, which provide an access disconnection sensor, which is integrated half in the arterial line 305 and half in the venous line 392 to detect access disconnection of the subject from the apparatus 300. An alternative embodiment for detection of accidental needle disconnections is the use of a conductive blanket underneath the subject's access. In such embodiments, the presence of blood changes the conductivity of the blanket and sets off an alarm and stops the pumps.

With reference to FIG. 1, a methodology of the type disclosed herein comprises establishing fluid communication between a subject's blood flow as accessed through a vein (e.g., jugular, subclavian or femoral veins) of the subject 355 and the inlet 305 of the apparatus 300. Alternatively the subject's blood flow may be accessed via one or more chronic vascular accesses. For example, a chronic vascular access may have been created by a surgical procedure: such as (i) native arteriovenous fistulas (native AVFs), (ii) arteriovenous shunts using graft material (AV graft), and (iii) tunnelled double-lumen catheters. The pump 360 regulates the flow of the subject's blood to the remainder of the apparatus 300 through conduit 315. Conduit 315 may be a pipe or flow line comprised of material suitable for use in the methodologies disclosed herein. In an embodiment, the subject's blood is allowed to flow through conduit 315 until it reaches valve 380 which when in the on position allows the blood flow to enter column A 310 in a particular flow direction 390. Blood may be pumped through column A 310 and exit the column thorough an outlet regulated by a valve 385. Blood exiting from column A 310 through the outlet regulated by valve 385 may enter conduit 395 where it is pumped to inlet port 340 whose access is regulated by valve 345. When valve 345 is in the on position, the blood may be pumped from inlet port 340 to column B 350 where it moves in flow direction G 342 through column B 350 to outlet port 348 which is regulated by valve 352. When valve 352 is in the on position the blood may flow from column B 350 into conduit 315. In an embodiment, the subject's blood is allowed to flow through conduit 315 until it reaches inlet port 360 which is regulated by valve 362 which when in the on position allows the blood flow to enter column C 370 in a particular flow direction H 375. The blood may exit column C 370 via outlet port 378 which is regulated by valve 376 which when in the on position allows the blood to flow into conduit 395 and back to the vein of the subject 392.

In an embodiment, the rate of flow of a bodily fluid (e.g., blood) through apparatus 300 may be regulated to provide some user and/or process goal. For example, the rate of blood flow through apparatus 300 may range from about 1 mL/min to about 300 mL/min, alternatively from about 25 mL/min to about 300 mL/min, alternatively from about 25 mL/min to about 150 mL/min, or alternatively from about 150 mL/min to about 300 mL/min. In an embodiment, treatment of a subject suffering from a VISE may require the subject be in fluid communication with apparatus 300 for a period of time ranging from about 1 hour to about 24 hours, alternatively from about 1 hour to about 12 hours, alternatively from about 1 hour to about 6 hours, alternatively from about 1 hour to about 4 hours, or alternatively less than about 4 hours. In an embodiment, the subject is in fluid communication with the apparatus 300 for a time period sufficient to allow from about 0.5 to about 10× the total blood volume of the subject to circulate through the apparatus 300. Alternatively, from about 1 to about 10× the total blood volume of the subject is allowed to circulate through the apparatus. In yet another embodiment, the blood volume circulated through the apparatus (e.g., apparatus 300) may range from about 5 liters to about 72 liters, alternatively form about 10 liters to about 60 liters, or alternatively from about 36 liters to about 54 liters and may occur in a time period ranging from about 1 hour to about 6 hours or alternatively from about 3 hours to about 4 hours. In some embodiments, the subject suffering from the VISE (e.g., Ebola) may undergo treatments where they are placed in fluid communication with the apparatus a plurality of times as deemed sufficient to address their particular disease state.

It is to be understood that FIG. 1 presents an embodiment of an apparatus suitable for use in the present disclosure. Additional routine modifications to the apparatus are contemplated by the present disclosure. For example, the apparatus may contain more or less than the 3 columns depicted in FIG. 1 or the columns may be disposed in positions other than perpendicular to conduits 315 and 395. In an embodiment, the apparatus 300 may be associated with a computer system.

Figure 2:
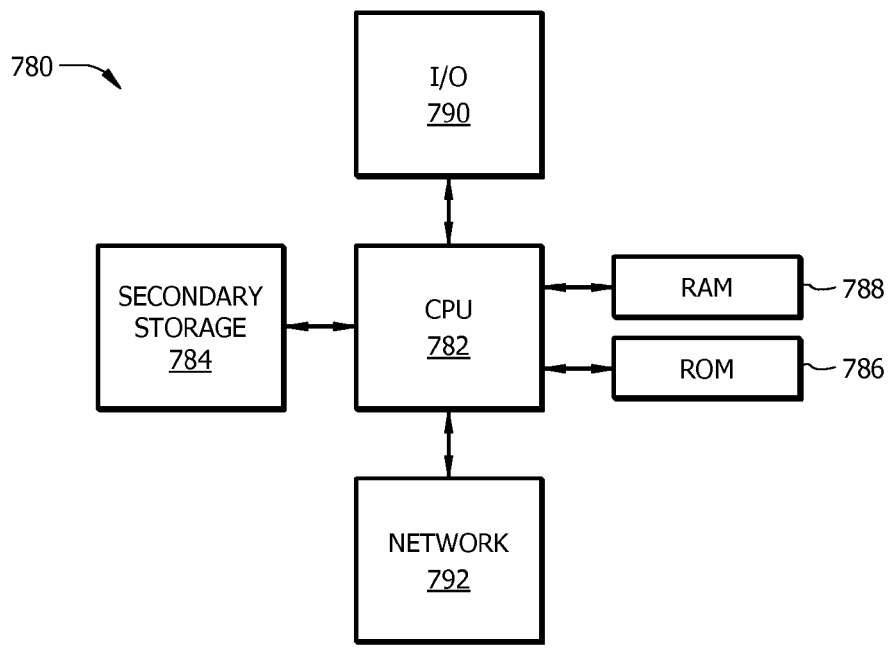
Figure 3A:
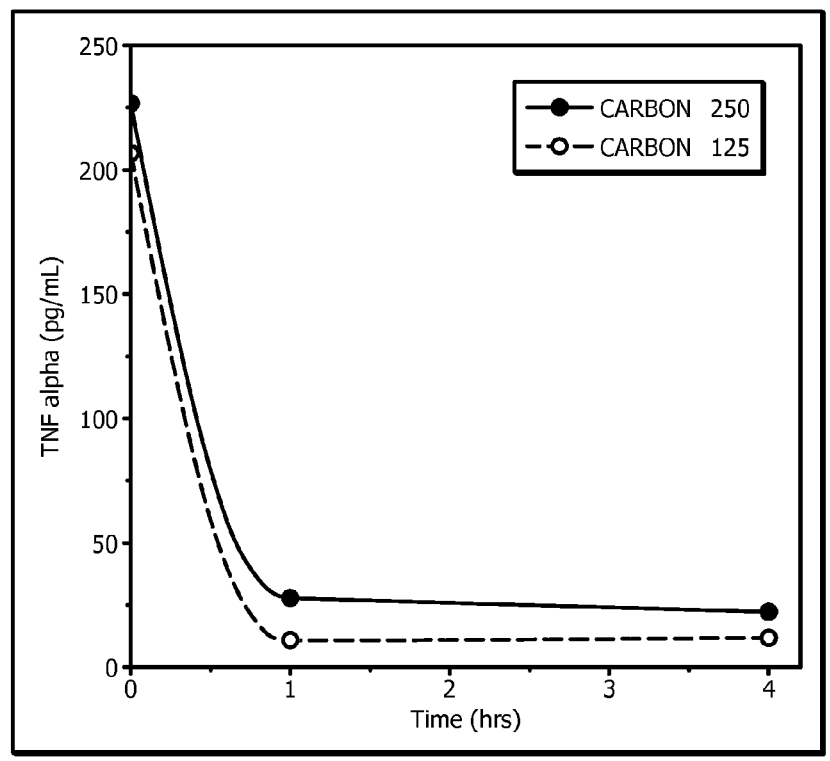
FIG. 3A is a plot of the amount of TNFα in a sample of fresh frozen plasma as a function of time following contact with the indicated adsorbent.
Figure 3B:
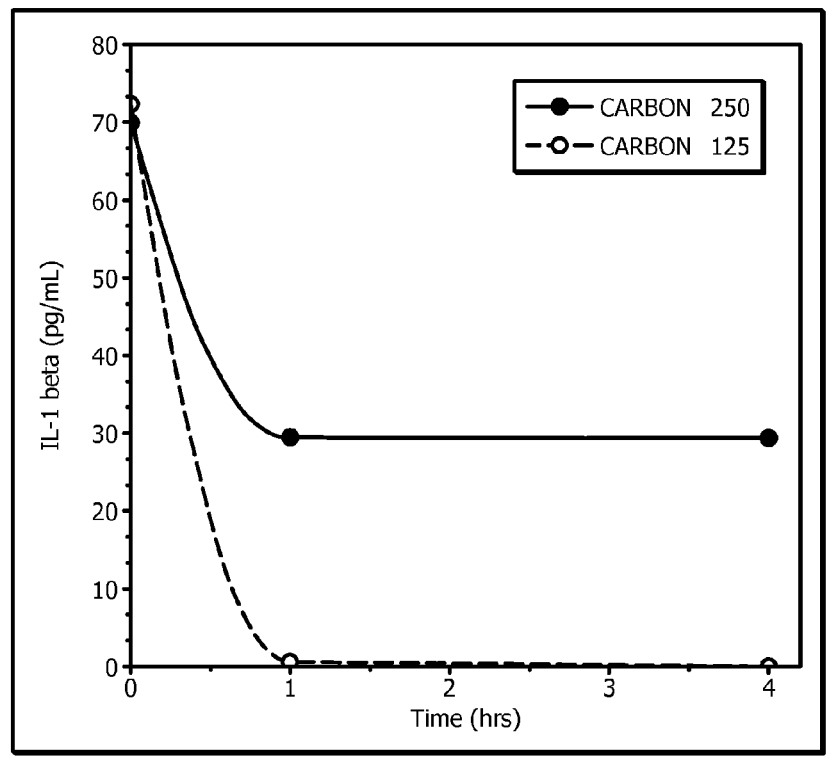
FIG. 3B is a plot of the amount of IL-1β in a sample of fresh frozen plasma as a function of time following contact with the indicated adsorbent.
Figure 3C:
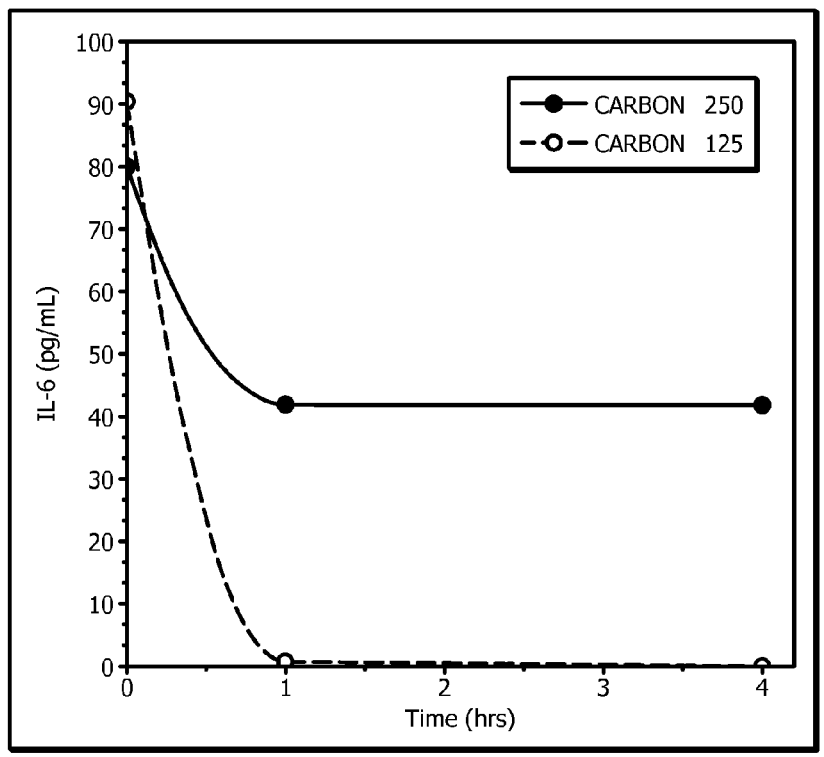
FIG. 3C is a plot of the amount of IL-6 in a sample of fresh frozen plasma as a function of time following contact with the indicated adsorbent.
Figure 3D:
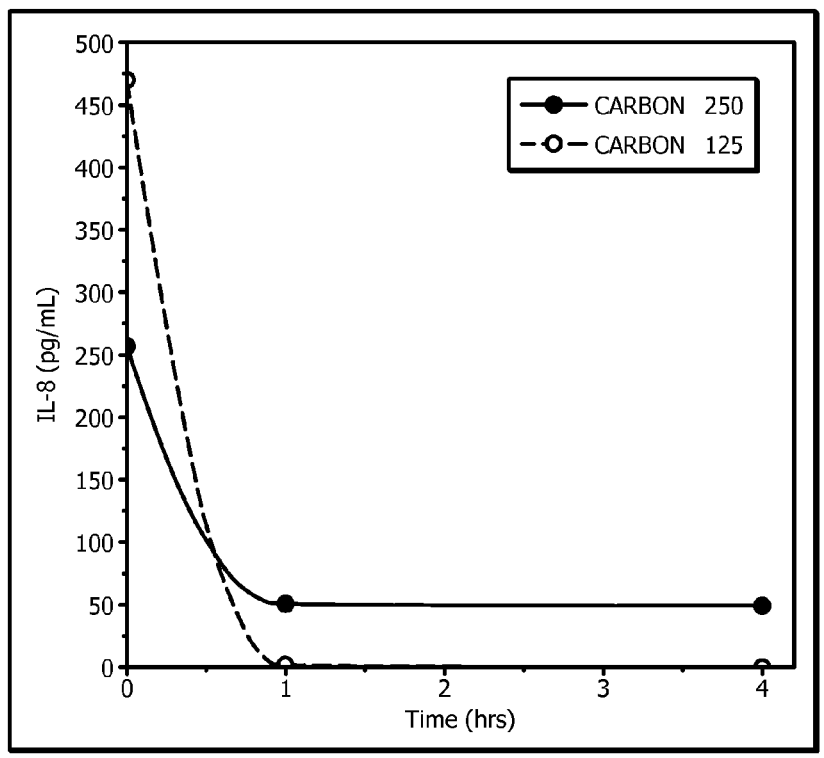
FIG. 3D is a plot of the amount of IL-8 in a sample of fresh frozen plasma as a function of time following contact with the indicated adsorbent.
Figure 3E:
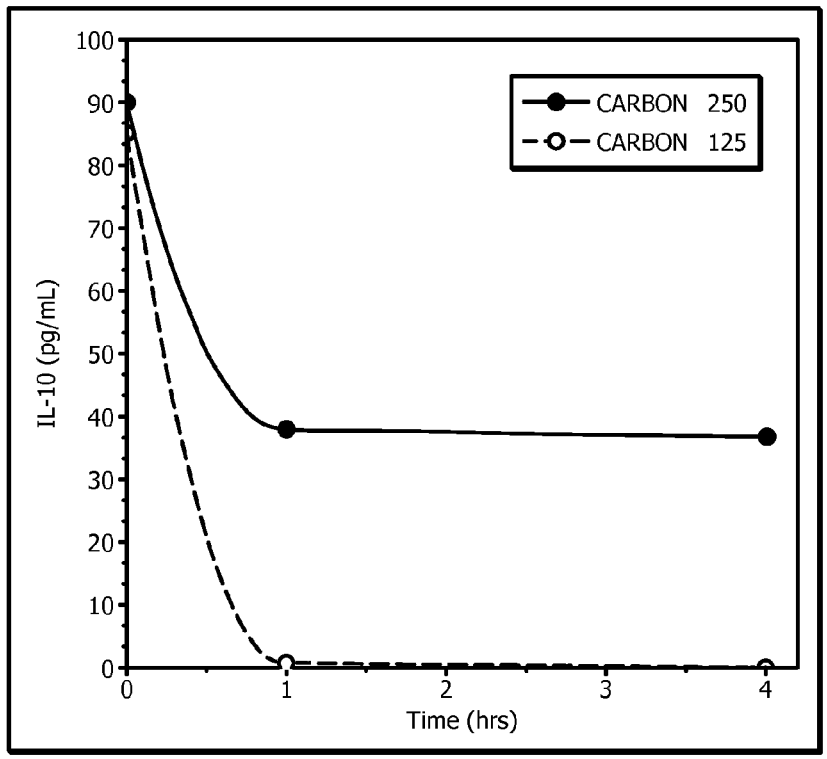
FIG. 3E is a plot of the amount of IL-10 in a sample of fresh frozen plasma as a function of time following contact with the indicated adsorbent.
Figure 3F:
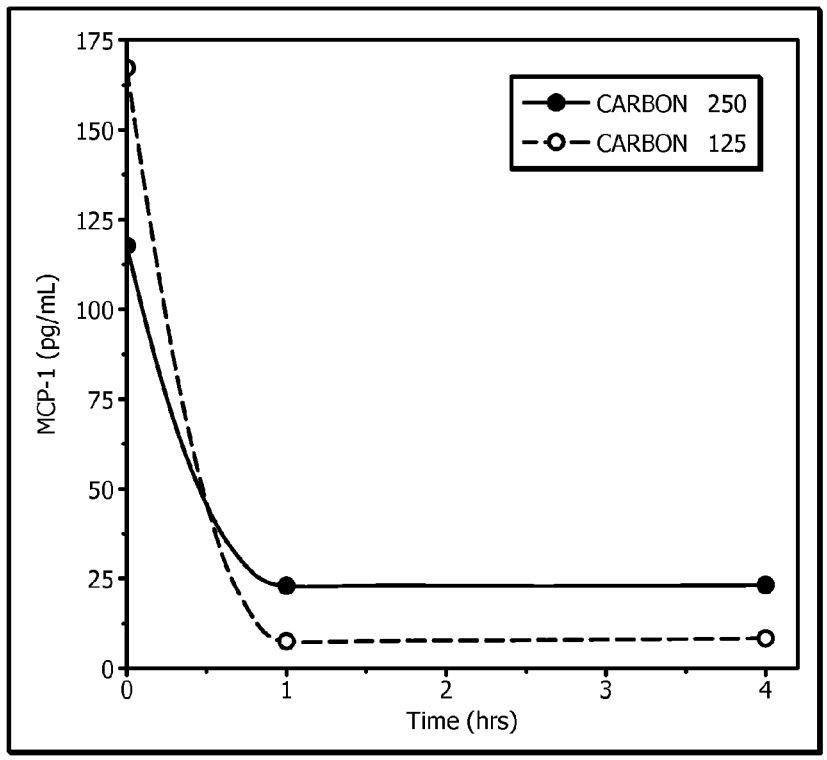
FIG. 3F is a plot of the amount of MCP-1 in a sample of fresh frozen plasma as a function of time following contact with the indicated adsorbent.
Figure 3G:
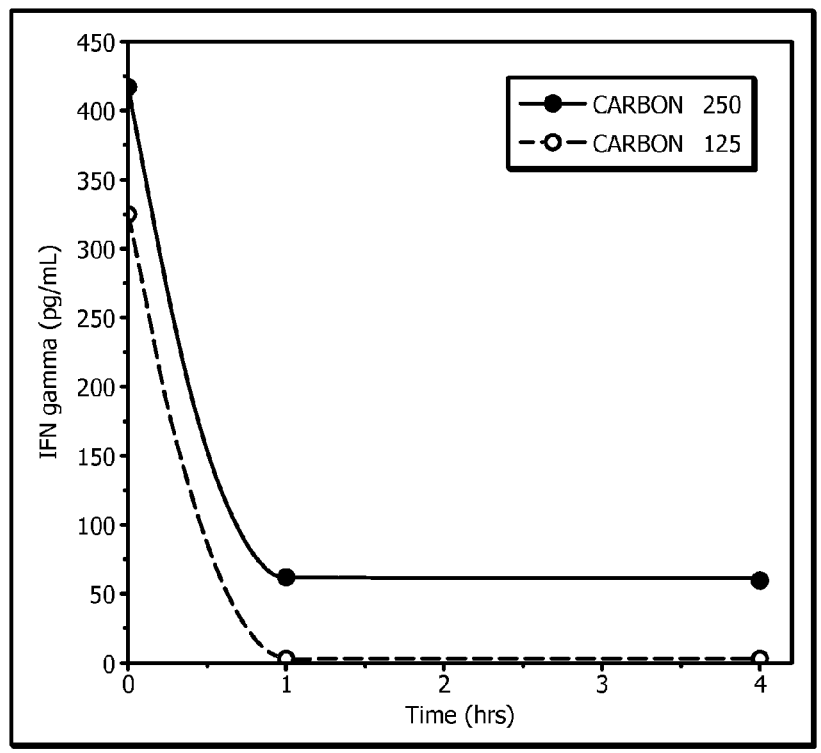
FIG. 3G is a plot of the amount of IFNγ in a sample of fresh frozen plasma as a function of time following contact with the indicated adsorbent.
Figure 3H:
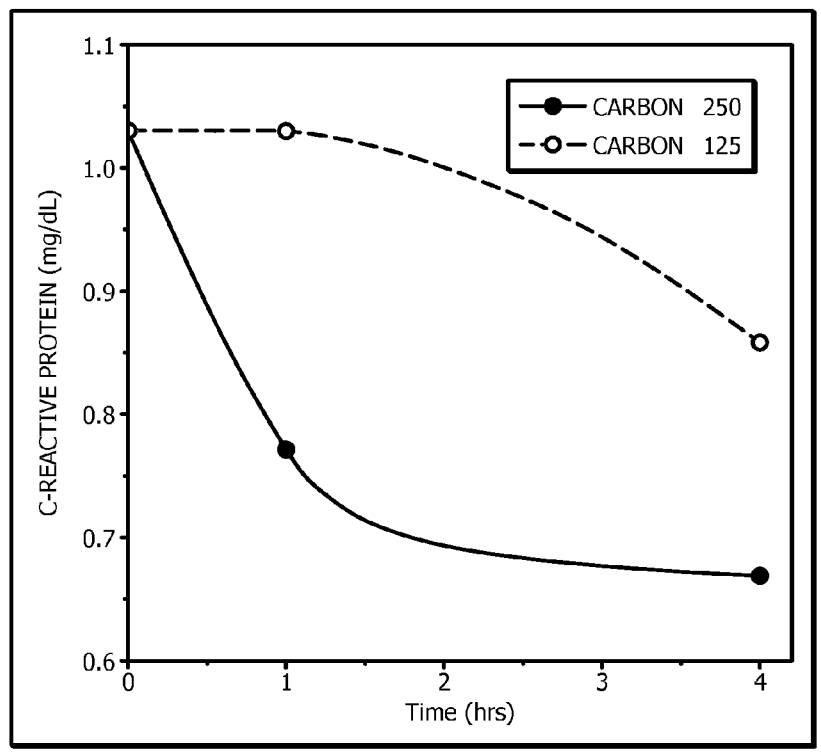
FIG. 3H is a plot of the amount of C-reactive protein in a sample of fresh frozen plasma as a function of time following contact with the indicated adsorbent.

FIG. 2 illustrates a computer system 780 suitable for implementing one or more embodiments disclosed herein. The computer system 780 includes a processor 782 (which may be referred to as a central processor unit or CPU) that is in communication with memory devices including secondary storage 784, read only memory (ROM) 786, random access memory (RAM) 788, input/output (I/O) devices 790, and network connectivity devices 792. The processor 782 may be implemented as one or more CPU chips.

It is understood that by programming and/or loading executable instructions onto the computer system 780, at least one of the CPU 782, the RAM 788, and the ROM 786 are changed, transforming the computer system 780 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 784 is typically comprised of one or more disk drives or tape drives and is used for non-volatile storage of data and as an over-flow data storage device if RAM 788 is not large enough to hold all working data. Secondary storage 784 may be used to store programs which are loaded into RAM 788 when such programs are selected for execution. The ROM 786 is used to store instructions and perhaps data which are read during program execution. ROM 786 is a non-volatile memory device which typically has a small memory capacity relative to the larger memory capacity of secondary storage 784. The RAM 788 is used to store volatile data and perhaps to store instructions. Access to both ROM 786 and RAM 788 is typically faster than to secondary storage 784. The secondary storage 784, the RAM 788, and/or the ROM 786 may be referred to in some contexts as computer readable storage media and/or non-transitory computer readable media.

I/O devices 790 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 792 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 792 may enable the processor 782 to communicate with an Internet or one or more intranets. With such a network connection, it is contemplated that the processor 782 might receive information from the network, or might output information to the network in the course of performing the above-described method steps. Such information, which is often represented as a sequence of instructions to be executed using processor 782, may be received from and outputted to the network, for example, in the form of a computer data signal embodied in a carrier wave.

Such information, which may include data or instructions to be executed using processor 782 for example, may be received from and outputted to the network, for example, in the form of a computer data baseband signal or signal embodied in a carrier wave. The baseband signal or signal embodied in the carrier wave generated by the network connectivity devices 792 may propagate in or on the surface of electrical conductors, in coaxial cables, in waveguides, in an optical conduit, for example an optical fiber, or in the air or free space. The information contained in the baseband signal or signal embodied in the carrier wave may be ordered according to different sequences, as may be desirable for either processing or generating the information or transmitting or receiving the information. The baseband signal or signal embodied in the carrier wave, or other types of signals currently used or hereafter developed, may be generated according to several methods well known to one skilled in the art. The baseband signal and/or signal embedded in the carrier wave may be referred to in some contexts as a transitory signal.

The processor 782 executes instructions, codes, computer programs, scripts which it accesses from hard disk, floppy disk, optical disk (these various disk based systems may all be considered secondary storage 784), ROM 786, RAM 788, or the network connectivity devices 792. While only one processor 782 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 784, for example, hard drives, floppy disks, optical disks, and/or other device, the ROM 786, and/or the RAM 788 may be referred to in some contexts as non-transitory instructions and/or non-transitory information.

In an embodiment, the computer system 780 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 780 to provide the functionality of a number of servers that is not directly bound to the number of computers in the computer system 780. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 780, at least portions of the contents of the computer program product to the secondary storage 784, to the ROM 786, to the RAM 788, and/or to other non-volatile memory and volatile memory of the computer system 780. The processor 782 may process the executable instructions and/or data structures in part by directly accessing the computer program product, for example by reading from a CD-ROM disk inserted into a disk drive peripheral of the computer system 780. Alternatively, the processor 782 may process the executable instructions and/or data structures by remotely accessing the computer program product, for example by downloading the executable instructions and/or data structures from a remote server through the network connectivity devices 792. The computer program product may comprise instructions that promote the loading and/or copying of data, data structures, files, and/or executable instructions to the secondary storage 784, to the ROM 786, to the RAM 788, and/or to other non-volatile memory and volatile memory of the computer system 780.

In some contexts, a baseband signal and/or a signal embodied in a carrier wave may be referred to as a transitory signal. In some contexts, the secondary storage 784, the ROM 786, and the RAM 788 may be referred to as a non-transitory computer readable medium or a computer readable storage media. A dynamic RAM embodiment of the RAM 788, likewise, may be referred to as a non-transitory computer readable medium in that while the dynamic RAM receives electrical power and is operated in accordance with its design, for example during a period of time during which the computer 780 is turned on and operational, the dynamic RAM stores information that is written to it. Similarly, the processor 782 may comprise an internal RAM, an internal ROM, a cache memory, and/or other internal non-transitory storage blocks, sections, or components that may be referred to in some contexts as non-transitory computer readable media or computer readable storage media.

In an embodiment, adsorbent materials are disposed within or contained by the columns of apparatus 300. Adsorbent materials suitable for use in the present disclosure include chromatographic materials, which have been subjected to a sanitization process. In an embodiment, the adsorbent materials are selected from the group consisting of synthetic carbon, anion exchange resins, cation exchange resins, and combinations thereof.

In an embodiment, the adsorbent material comprises synthetic carbon particles (SCP) containing micro-, meso- and macropores from porous phenolic resins. As used herein, the term "micropore" refers to a pores with diameter <2 nm, as measured by nitrogen adsorption and mercury porosimetry methods and as defined by IUPAC. As used herein, the term "mesopore" refers to pores with diameter from ca. 2 nm to ca. 50 nm, as measured by nitrogen adsorption and mercury porosimetry methods and as defined by IUPAC. As used herein, the term "micropore" refers to pores with diameters larger than 50 nm, as measured by nitrogen adsorption and mercury porosimetry methods and as defined by IUPAC. In relation to this disclosure there are two types of macropores. In macroporous beads they are located within beads and formed by pore-formers. Their size is 50-500 nm, typically 70-200 nm. These macropores are very effective in adsorption of cytokines.

A SCP suitable for use in the present disclosure may have any shape compatible with the compositions and methodologies disclosed herein. For example the shape of the SCP may be that of an irregular granule, a low angularity shape, spherical (e.g., bead), pellet, minilith, monolith, etc. . . . . For simplicity, the present disclosure may refer to the use of beads of the SCB however it is to be understood the SCP may be of any suitable shape. The SCPs may be formed using any suitable methodology to results in a material having the properties disclosed herein. In an exemplary method for the formation of an SCP, a precursor resin formulation is used which comprises a large proportion of pore former, e.g. 250 parts ethylene glycol or other pore former to 100 parts of resin-forming components.

Herein a mesoporous resin may be formed by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso- or macroporosity to the resin (e.g. at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-800 $m^2/g$ without activation. It may be activated by heating it at high temperature in the presence of carbon dioxide, steam or a mixture thereof, e.g. by heating it in carbon dioxide at above 800° C., or it may be activated by heating it in air at above 400° C. It may then have surface areas of up to 2000 $m^2/g$ and even higher e.g. 1000-2000 $m^2/g$. As used herein the term "BET surface area" is determined by the Brunauer, Emmett, and Teller (BET) method according to ASTM D1993-91, see also ASTM D6556-04.

Resins for making carbonaceous material can be prepared from any of the starting materials such that the nucleophilic components may comprise phenol, bisphenol A, alkyl phenols e.g. cresol, diphenols e.g. resorcinol and hydroquinione and aminophenols e.g. m-amino-phenol.

It is preferred to use as nucleophilic component a phenolic novolac or other similar oligomeric starting material, which because it is already partly polymerized makes polymerization to the desired resin a less exothermic and hence more controllable reaction. The preferred novolacs have average molecular weights (AMW) in the range of from 300 to 3000 prior to cross-linking (corresponding to a DP with respect to phenol of about 3-30). Where novolac resins are used, they may be solids with melting points in the region of 100° C. Novolac resins of AMW less than 2000 and preferably less than 1500 form resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble. Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to: (a) Dihydric phenols e.g. resorcinol and hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins. (b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid or phthalic acid. The concentration of novolac in the pore former may be such that when combined with the solution of cross-linking agent in the same pore former the overall weight ratio of pore former to (novolac+cross-linking agent) is at least 125:100 by weight. The actual ratios of novolac:pore former and cross-linking agent:pore former are set according to convenience in operation by the operational requirements of a bead production plant and are controlled by the viscosity of the novolac:pore former solution such that it remains pumpable and by the ratio of cross-linking agent:pore former such that the cross-linking agent remains in solution throughout the plant.

The cross-linking agent is normally used in an amount of from 5 to 40 parts by weight (pbw) per 100 parts by weight of the nucleophilic components e.g. novolac. It may be, for example, an aldehyde e.g. formaldehyde or furfural, it could be hexamethylenetetramine (hexamine), or hydroxymethylated melamine.

Hexamine is preferably used as cross-linking agent. In embodiments requiring a completely cured resin, it is preferably used for cross-linking novolac resin at a proportion of 10 to 25 pbw e.g. about 15 to 20 pbw hexamine per 100 pbw of novolac. This ensures formation of the solid resin with maximal cross-linking degree and ensures the stability of the mesopore structure during subsequent removal of the pore former.

The pore former also acts as solvent. Thus, the pore former is preferably used in sufficient quantities to dissolve the components of the resin system, the weight ratio of pore former to the total components of the resin system resin being preferably at least 1.25:1.

The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, .gamma.-butyrolactone, propylene carbonate, dimethylformamide, N-methyl-2-pyrrolidinone and monoethanolamine, ethylene glycol being preferred, and where the selection is also limited by the thermal properties of the solvent as it should not boil or have an excessive vapour pressure at the temperatures used in the curing process.

It is thought that the mechanism of meso- and macropore generation is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lighter pre-polymer trapped between the domains. In the presence of a low level of pore former the pore former is compatible with, and remains within, the cross-linked resin domains, (e.g., <120 parts/100 parts Novolac for the Novolac-Hexamine-Ethylene Glycol reaction system), whilst the remainder forms a solution with the partially cross-linked polymer between the domains. In the presence of higher levels of pore former, which exceed the capacity of the cross-linked resin, the pore former adds to the light polymer fraction increasing the volume of material in the voids between the domains that gives rise to the mesoporosity and/or macroporosity. In general, the higher the pore former content, the wider the mesopores, up to macropores, and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), the presence of water within the solvent and concentration of any curing catalyst if present.

Production of the bead form may be by pouring a solution of a partially cross-linked pre-polymer into a hot liquid such as mineral oil containing a dispersing agent and stirring the mixture. The pre-polymer solution forms into beads which are initially liquid and then, as curing proceeds, become solid. The average bead particle size is controlled by several process parameters including the stirrer type and speed, the oil temperature and viscosity, the pre-polymer solution viscosity and volume ratio of the solution to the oil and the mean size can be adjusted between 5 and 2000 μm although in practice the larger bead sizes are difficult to achieve owing to problems with the beads in the stirred dispersion vessel. The beads can then be filtered off from the oil. In a preparative example, industrial novolac resin is mixed with ethylene glycol at an elevated temperature, mixed with hexamine and heated to give a viscous solution which is poured into mineral oil containing a drying oil, after which the mixture is further heated to effect curing. On completion of curing, the reaction mixture is cooled, after which the resulting porous resin is filtered off, and washed with hot water to remove pore former and a small amount of low molecular weight polymer. The cured beads are carbonized to porous carbon beads which have a pore structure as indicated above, and may be activated as indicated above. It is stated that the beads can be produced with a narrow particle size distribution e.g. with a D90.D10 of better than 10 and preferably better than 5. However, the bead size distribution that can be achieved in practice in stirred tank reactors is relatively wide, and the more the process is scaled up the worse the homogeneity of the mixing regime and hence the particle size distribution becomes wider.

Discrete solid beads of polymeric material e.g. phenolic resin having a porous structure may be formed, which process may produce resin beads on an industrial scale without aggregates of resin building up speedily and interrupting production. The process comprises the steps of: (a) combining a stream of a polymerizable liquid precursor e.g. a novolac and hexamine as cross-linking agent dissolved in a first polar organic liquid e.g. ethylene glycol with a stream of a liquid suspension medium which is a second non-polar organic liquid with which the liquid precursor is substantially or completely immiscible e.g. transformer oil containing a drying oil; (b) mixing the combined stream to disperse the polymerizable liquid precursor as droplets in the suspension medium e.g. using an in-line static mixer; (c) allowing the droplets to polymerise in a laminar flow of the suspension medium so as to form discrete solid beads that cannot agglomerate; and (d) recovering the beads from the suspension medium.

For bead production, the pore former comprises a polar organic liquid e.g. ethylene glycol chosen in combination with dispersion medium which is a non-polar organic liquid so as to form a mainly or wholly immiscible combination, the greater the incompatibility between the pore former which forms the dispersed phase and the dispersion medium, the less pore former becomes extracted into the dispersion medium. The pore former desirably has a greater density than the dispersion medium with which it is intended to be used so that droplets of the pore former containing dissolved resin-forming components will pass down a column more rapidly than a descending flow of dispersion medium therein. Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin beads by washing.

The dispersion medium is a liquid which can be heated to the temperature at which curing is carried out e.g. to 160° C. without boiling at ambient pressure and without decomposition and which is immiscible with ethylene glycol and with the dissolved components therein. It may be hydrocarbon-based transformer oil which is a refined mineral oil and is a by-product of the distillation of petroleum. It may be composed principally of C.15-C.40 alkanes and cycloalkanes, have a density of 0.8-0.9 depending upon grade and have a boiling point at ambient pressure of 260-330° C., also depending upon grade. Transformer oil has a viscosity of about 0.5 poise at 150° C. which is a typical cure temperature. Transformer oil or other dispersion medium may be used in volumes 3-10 times the volume of the combined streams of nucleophilic precursor and crosslinking agent e.g. about 5 times.

Preferred dispersing agents which are dissolved in the dispersion medium before that medium is contacted with the reaction mixture to be dispersed therein to retard droplet coalescence are either sold as drying oils e.g. Danish oil or are produced by partially oxidizing naturally occurring precursors such as tung oil, linseed oil etc. The dispersing agents are consumed as the process proceeds, so that if the dispersion medium is recycled, dispersing agent in the recycled oil stream should be replenished. The dispersing agent is conveniently supplied as a stream in solution in the dispersion medium e.g. transformer oil and e.g. in an amount of 5-10% v/v where Danish oil is used which contains a low concentration of the active component to give final concentration of the dispersant in the dispersion medium 0.2-1% v/v. Higher dispersant concentrations would be used in the case of oxidised vegetable oils.

The resin beads formed as described above may be carbonised and optionally activated. For example, carbonization and activation may comprise supplying the material to an externally fired rotary kiln maintained at carbonizing and activating temperatures, the kiln having a downward slope to progress the material as it rotates, the kiln having an atmosphere substantially free of oxygen provided by a counter-current of steam or carbon dioxide, and annular weirs being provided at intervals along the kiln to control progress of the material. In an embodiment, a SCP suitable for use in the present disclosure is characterized by a microporous/macroporous structure.

In an embodiment, the SCP has a macroporous pore size of from about 75 µm to about 1000 µm, alternatively the SCP has a macroporous size of from about 100 µm to about 750 µm, or alternatively from about 100 µm to about 500 µm. Herein an SCP suitable for use in the present disclosure may comprise an SCP having at least two pore size distribution such that the SCP is a mixture of carbon beads having at least two distributions of macroporous pore sizes. In an embodiment, the SCP may comprise a first population having a macroporous pore size denoted x and a second population having a macroporous pore size y where the SCP provides a mixture having a ratio of x/y of about 1; alternatively about 5, alternatively about 10, alternatively about 20; alternatively about 50, or alternatively about 100. In some embodiments, the SCP comprises a mixture of two populations wherein the pore size of the first population is approximately twice the pore size of the second population. In some embodiments, the SCP comprises a mixture of three populations where the pore size of a first population is approximately twice the pore size of the second population and the pore size of the third population is approximately two and a half times the pore size of the second population.

In an embodiment, the adsorbent material comprises an ion exchange resin (IER). Herein an IER refers to an insoluble matrix fabricated from a substrate and functionalized with a fixed ion and a mobile counterion. The IER retards ions on the surface of the material with the concomitant release of the mobile counterion. IERs can also be described as insoluble polymers that contain ionizable groups distributed regularly along the polymer backbone. As a consequence, any counter ion associated with the ion exchange resin is ionically bound to the ion exchange resin and physically separated from the surrounding fluid.

In an embodiment, an IER suitable for use in the present disclosure has a bead size ranging from about 40 µm to about 1000 µm, alternatively from about 40 µm to about 750 µm, or alternatively from about 100 µm to about 500 µm.

In an embodiment, the IER is an anion exchange resin. Herein "anion exchange resin" refers to an ion exchange resin with covalently bound positively charged groups, such as quaternary amino groups and mobile negatively charged groups. The term "anion exchange resin" is intended to encompass strong base anion exchange resins (SBA), weak base anion exchange resins (WBA) and related anionic functional resins, of either the gellular or macroporous type containing quaternary ammonium functionality (chloride, hydroxide or carbonate forms), dialkylamino or substituted dialkylamino functionality (free base or acid salt form), and aminoalkylphosphonate or iminodiacetate functionality, respectively. Examples of commercially available anion exchange resins suitable for use in the present disclosure include without limitation those sold under the tradename of DEAE, QAE, and UNOSphere. In an embodiment, the anion exchange resin comprises UNOSphere Q Media.

In an embodiment, the IER is a cation exchange resin. The cation exchange resin of the present disclosure may be strongly or weekly acidic and have a variety of functional groups, e.g., weakly acidic type of resin containing carboxylic acid group, or strongly acidic type of resin containing sulfonic functional groups. Generally, the carboxylic functional groups may be derived from polymers or copolymers of methacrylic acid or polymethacrylic acid and the sulfonic functional groups may generally be derived from polymers or copolymers of styrene and divinylbenzene. Other polymeric matrices, organic ion exchange matrices or inorganic ion exchange matrices may be used as suitable ion exchange resins, e.g., methacrylic, acrylic and phenol formaldehyde. For example, cation exchange resins suitable for use in the present disclosure include without limitation AMBERLITE and UNOSphere S Media. AMBERLITE is described by the manufacturer as gel-type divinylbenzene sulfonic acid cation exchange resin that swells in water.

In an embodiment, an adsorbent material suitable for use in the present disclosure has been subjected to a sanitization process. Herein the sanitization process refers to a method of treating the adsorbent materials in order to (i) remove pathogens; (ii) reduce the amount of fine particulates and leachables; (iii) reduce the amount of trapped air and (iv) sterilize the materials. Adsorbent materials that have been subjected to the sanitization process disclosed herein are considered to have been converted from an industrial grade material to a pharmaceutical grade material with a concomitant increase in hemocompatability.

In an embodiment, a method for sanitization of a SCP of the type disclosed herein comprises a dry heat treatment to produce a heat-treated SCP. Dry heat treatment of the SCP may be carried out at a temperature at equal to or greater than about 180° C. for a time period equal to or greater than about 4 hours, alternatively at a temperature of equal to or greater than about 200° C. for a time period of equal to or greater than about 1 hour, or alternatively at a temperature of 250° C. for a time period of equal to or greater than about 30 min. Dry heat treatment of the SCP may function to reduce the bioburden of the material and particularly the amount of pathogenic (e.g., bacteria, viruses, fungi, etc. . . . ) and pyrogenic (e.g., endotoxin) substances associated with the SCP. For example, the total amount of pathogenic substances associated with the heat-treated SCP may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the SCP.

In an embodiment, the bioburden of the SCP is reduced by about 100% through the use of a dry heat treatment. Alternatively, the bioburden of the SCP is reduced through the use of any suitable methodology compatible with the SCP and the other components of the present disclosure. In some embodiments, the bioburden of the SCP is reduced by 100% utilizing methodologies consistent with jurisdictional guidelines for the sanitization of materials that will contact mammalian blood and produce a product that will be subsequently utilized in mammals.

In an embodiment, a method for sanitization further comprises the removal of fine particulates and leachables from the heat-treated SCP. Herein particulates smaller than about 30 microns are referred to as "fines" while "leachables" describe the organic compounds that can be eluted from the adsorbent material (e.g., heat-treated SCP) in the presence/absence of an applied sample. In an embodiment, removal of the fine particulates and leachables from the heat-treated SCP comprises contacting the heat-treated SCP with water, removing water from the heat-treated SCP to produce a washed SCP, contacting the washed SCP with a salt solution to produce a modified SCP and removing the salt solution from the modified SCP to produce a processed SCP. The heat-treated SCP may be contacted with from about 4 volumes to about 10 volumes of water, alternatively from about 5 volumes to about 10 volumes of water or alternatively from about 6 volumes to about 8 volumes of water. Contacting of the adsorbent material with a substance may be carried out in any suitable vessel. For example, the adsorbent material (e.g., heat-treated SCP) may be positioned within a cartridge or column to facilitate contacting of the adsorbent material with one or more substances of the type disclosed herein. For example, the washed SCP may be contacted with a salt solution comprising a sodium chloride salt at a concentration of 3 g/dL. The washed SCP may be contacted with from about 4 volumes to about 10 volumes of salt solution based on the total volume of the SCP, alternatively from about 6 volumes to about 10 volumes of salt solution or alternatively from about 6 volumes to about 8 volumes of salt solution. It is contemplated that other salt solutions providing similar pH and osmolarity, such as known to the ordinarily skilled artisan and compatible with the other methods and compositions of the present disclosure, may be employed to facilitate the removal of fine particulates and leachables from the SCP.

For either the removal of water to produce a washed SCP or the removal of salt to produce a processed SCP, the removal may be effected using any suitable methodology. For example, the removal of fine particulates and leachables may be carried out by placing the adsorbent material in a column which may be allowed to drain under gravity until no further filtrate is detected in order to remove the water and/or salt solution. In some embodiments, the adsorbent material may be subjected to a plurality of processes for the removal of fine particulates and leachables. Further, in some embodiments, the solution produced by contacting the adsorbent material with water and/or a salt solution may be analyzed to determine the amount of fine particulates and/or leachables removed following contact. Such determinations may be made and the process for removal of fine particulates and/or leachables repeated until some user and/or process desired level of fine particulates and/or leachables is achieved.

In an embodiment, a method for sanitization further comprises dewatering the processed SCP. Water present with the adsorbent material has the tendency to separate from the material resulting in compaction and a reduction in flow properties. De-watering is the process of removing extraneous fluid (typically water or aqueous solutions) from wet or slurried particles without removing fluid in the particles (i.e., prevent evaporative drying of the particles). Herein "extraneous" means any fluid outside the particles. Therefore any fluid absorbed into the polymer matrix or present in the pores is not considered extraneous.

Any suitable methodology may be employed for the dewatering of the processed SCP. Examples of methodologies suitable for use in dewatering the processed SCP include without limitation the passage of air through the particles. The resultant material is referred to as the dewatered SCP. In an embodiment, dewatering of the processed SCP is carried out using a dewatering apparatus.

In an embodiment, a method for sanitization further comprises aseptic processing of the dewatered SCP, also referred to as sterile fill and sterilization to produce a sanitized SCP. Sterility may be achieved using any suitable methodology. For example sterile processing may include the use of clean rooms, bacteria retaining filters, and dry or steam heat. In an embodiment, aseptic processing of the dewatered SCP comprises terminal sterilization by autoclaving (e.g., at 121° C., 15 psi for 30 min), gas sterilization, e-beam sterilization, gamma radiation, or combinations thereof.

In an embodiment, the adsorbent material is an IER (e.g., anion exchange resin) and a method for sanitization of an IER comprises the removal of fine particulates. Removal of the fine particulates from the IER may comprise contacting the IER with water, removing water from the IER to produce a washed IER, contacting the washed IER with a salt solution to produce a modified IER and removing the salt solution from the modified IER to produce a processed IER. The IER may be contacted with from about 4 volumes to about 10 volumes of water based on the total volume of the IER, alternatively from about 6 volumes to about 10 volumes of water or alternatively from about 6 volumes to about 8 volumes of water. Contacting of the adsorbent material with a substance may be carried out in any suitable vessel. For example, the adsorbent material (e.g., IER) may be positioned within a cartridge or column to facilitate contacting of the adsorbent material with one or more substances of the type disclosed herein. In an embodiment, the washed IER is contacted with a salt solution comprising for example 0.9% NaCl in water. It is contemplated that other salt solutions, such as known to the ordinarily skilled artisan providing similar pH and osmolarity, and compatible with the other methods and compositions of the present disclosure, may be employed to facilitate the removal of fine particulates and leachables from the IER. The washed IER may be contacted with from about 2 volumes to about 8 volumes of salt solution based on the total volume of IER, alternatively from about 4 volumes to about 8 volumes of salt solution or alternatively from about 6 volumes to about 8 volumes of salt solution. For either the removal of water to produce a washed IER or the removal of salt to produce a processed IER, the removal may be effected using any suitable methodology. For example, the removal of fine particulates may be carried out by placing the adsorbent material in a column which may be allowed to drain under gravity until no further filtrate is detected in order to remove the water and/or salt solution. In some embodiments, the adsorbent material may be subjected to a plurality of processes for the removal of fine particulates. Further, in some embodiments, the solution produced by contacting the adsorbent material with water and/or a salt solution may be analyzed to determine the amount of fine particulates. Such determinations may be made and the process for removal of fine particulates repeated until some user and/or process desired level of fine particulates is achieved.

In an embodiment, a method for sanitization further comprises autoclaving the processed IER. Autoclaving of the processed IER may be carried out at a temperature of equal to or greater than about 121° C. for a period of time equal to or greater than about 30 min, alternatively equal to or greater than about 60 min, or alternatively for a period of time from about 30 min to about 60 min. The resultant material is termed an autoclaved IER.

The autoclaved IER may be further processed by undergoing a high pH treatment. For example, the autoclaved IER may be contacted with an about 0.5 M to about 2M NaOH solution for a period of time equal to or less than about 24 hours It is contemplated that other basic solutions providing the pH characteristics of a 0.5M-2M NaOH solution and compatible with the other aspects of this disclosure may be employed for high pH treatment of the IER. The resultant material is termed a pH-treated IER. Autoclaving of the processed IER may function to reduce the bioburden of the material and particularly the amount of pathogenic (e.g., bacteria, viruses, fungi, etc. . . . ) and pyrogenic (e.g., endotoxin) substances associated with the processed IER. For example, the total amount of pathogenic substances associated with the autoclaved IER may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the IER. In an embodiment, the bioburden of the IER is reduced by about 100% through the use of methodologies disclosed herein. Alternatively, the bioburden of the IER is reduced by about 100% through the use of any suitable methodology compatible with the IER and the other components of the present disclosure. In some embodiments, the bioburden of the IER is reduced by 100% utilizing methodologies consistent with jurisdictional guidelines for the sanitization of materials that will contact mammalian blood and produce a product that will be subsequently utilized in mammals.

In an embodiment, a method for sanitization further comprises the chromatographic removal of base and leachables from the pH-treated IER. For example, the IER may be disposed within a column and contacted with sufficient volumes of a low concentration salt solution to provide an filtrate having a neutral pH. In an embodiment the IER may be washed with a 3% NaCl solution until the filtrate has a pH ranging from about 7.4 to about 7.6. It is contemplated that other salt solutions, such as known to the ordinarily skilled artisan and compatible with the other methods and compositions of the present disclosure, may be employed to facilitate the removal of bases and leachables from the IER. The resultant material is termed a modified IER.

In an embodiment, a method for sanitization further comprises dewatering the modified IER to produce a dewatered IER. Herein dewatering refers to the removal of water from the adsorbent materials. Water present with the adsorbent material has the tendency to separate from the material resulting in compaction and a reduction in flow properties. Any suitable methodology may be employed for the dewatering of the IER. Examples of methodologies suitable for use in dewatering the IER are described herein with regards to dewatering of the SCP.

In an embodiment, a method for sanitization further comprises aseptic processing of the dewatered IER, also referred to as sterile fill and sterilization to produce a sanitized IER. Sterility may be achieved using any suitable methodology. For example sterile processing may include the use of clean rooms, bacteria retaining filters, dry or steam heat, terminal sterilization by autoclaving at 121° C., 15 psi for 30 min, gas sterilization, e-beam sterilization, gamma radiation, or combinations thereof. In some embodiments, methods for sanitization of the SCP, IER, or both do not comprise or alternatively exclude aseptic processing.

The sanitization process disclosed herein may be performed using any suitable equipment and/or having the adsorbent material disposed within any suitable vessel for performing one or more steps of the sanitization process. In an embodiment, the adsorbent material is disposed within a column and the sanitization process is carried out without transfer of the adsorbent material to another container or vessel. In such embodiments, the adsorbent material is subjected to sanitization-in-place (SIP).

In an embodiment, adsorbent materials subjected to a sanitization process, both of the type disclosed herein, are characterized by a bioburden maximum of 20 endotoxin units (EU)/blood/plasma contacting device and 2.15 endotoxin units (EU)/CSF contacting device as determined using any suitable methodology such as the *Limulus* amebocyte lysate test. In an embodiment, adsorbent materials subjected to a sanitization process, both of the type disclosed herein, are characterized as fine particulates free which are defined herein as having less than about 1% fine particulates as determined by laser diffraction. Methodologies of the type disclosed herein may result in in adsorbent materials having less than about 0.5%, 0.1% or undetectable amounts of fine particulates. In an embodiment, adsorbent materials subjected to a sanitization process, both of the type disclosed herein, are characterized as leachables free which are defined herein as having less than about 1% leachables as determined spectrophotometrically in the wavelength range of 205 nm to 340 nm. Methodologies of the type disclosed herein may result in adsorbent materials having less than about 0.5%, 0.1% or undetectable amounts of leachables. Such materials are collectively referred to herein as sanitized adsorbent materials (SAM).

In an embodiment, the SAM is sanitized in accordance with the United States Food and Drug Administration Code of Federal Regulations Title 21 section 876.5870 for the regulation of Sorbent and Hemoperfusion systems.

In an embodiment, SAMs suitable for use in the present disclosure (e.g., in the columns of apparatus 300) are further subjected to contact with a compatibilizer which functions to coat at least a portion of the surface area of the SAM. Herein a compatibilizer refers to a substance that functions to increase the biocompatibility of the SAM with biological fluids and may aid in decreasing the binding of non-target molecules to the SAM. In an embodiment, the compatibilizer comprises a polysaccharide, a glucan, albumin, mannitol, a starch, or combinations thereof.

In an embodiment, the compatibilizer comprises dextran. Dextrans, representations are depicted in Formula 1, are polysaccharides having a linear backbone of α-linked D-glucopyranosyl repeating units. In an embodiment, a dextran suitable for use in the present disclosure has an average molecular weight ranging from about 1 kDa to about 500 kDa, alternatively from about 1 kDa to about 70 kDa, alternatively from about 1 kDa to about 40 kDa, or alternatively from about 40 kDa to about 70 kDa. Nonlimiting examples of compatibilizers suitable for use in the present disclosure include DEXTRAN-1, DEXTRAN-40 and DEXTRAN-70 commercially available from Hospira Inc.

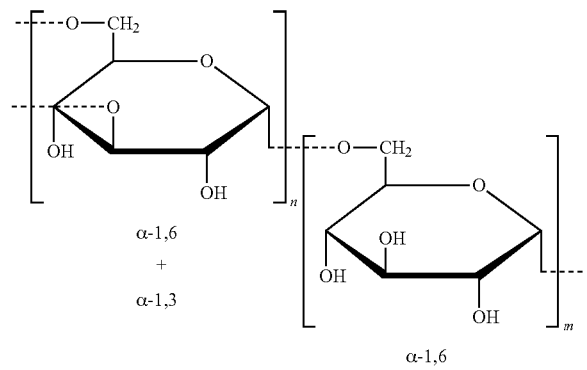

Formula I

In an embodiment, the compatibilizer comprises hydroxyethyl starch. Hydroxyethyl starch, depicted in Formula II, is a nonionic starch derivative that is commonly used as a volume expander in a type of intravenous therapy that has the function of providing volume for the circulatory system.

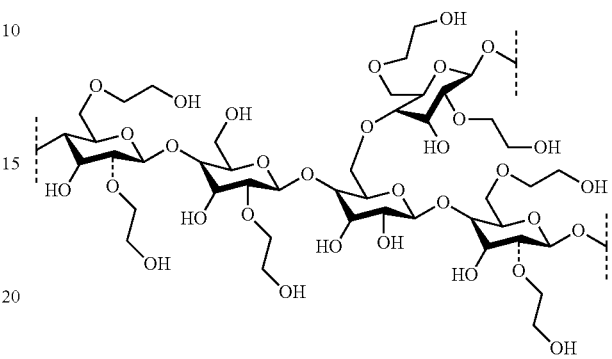

Formula II

In an embodiment the compatiblizer comprises a mixture of albumin and mannitol. Serum albumin is the main protein of human blood plasma whose primary function is to regulate the colloidal osmotic pressure of blood. Mannitol, (2R,3R,4R,5R)-Hexan-1,2,3,4,5,6-hexol, is a sugar alcohol, which can function an Osmotic Diuretic. The weight ratio of albumin to mannitol in the compatibilizer may range from 20:1 to 1:1, alternatively from 18:1 to 1:1, or alternatively from 15:1 to 10:1.

Without wishing to be limited by theory, the compatibilizer (e.g., dextran) may function to prime the extracorporeal circuit (i.e., apparatus having columns containing the adsorbent materials) and may lessen complications by blocking the initial exposure of blood components and plasma to foreign surfaces while maintaining a higher level of colloid oncotic pressure. In an embodiment, the compatibilizer is dextran 40 which may function in (i) preventing shear-induced fines formation via a lubrication effect; (ii) serving as a priming agent for the extracorporeal circuit assembled with the blood separator and the adsorbing device to prevent activation of plasma and other blood components following early primary exposure; and (iii) modulating sorbing capacity of porous sorbents such as synthetic mesoporous/microporous carbon. For example, the adsorbents packed into columns as components of an apparatus of the type disclosed herein, during storage/distribution can be exposed to relatively high shear stresses which can be a continuous source of particulates while dextran may prevent fines formation by lubrication at any shear condition.

SAMs suitable for use in the present disclosure may be contacted with the compatibilizer using any suitable methodology. In an embodiment, the compatibilizer is dextran which may be formulated as a solution suitable for use in the present disclosure having from about 1 weight percent (wt. %) dextran about 10 wt. % dextran, alternatively from about 2 wt. % to about 9 wt. % or alternatively from about 3 wt. % to about 7 wt. %. In an embodiment, the compatibilizer is hydroxyethyl starch which may be formulated as a solution suitable for use in the present disclosure having from about 1 wt. % to about 6 wt. % hydroxyethyl starch, alternatively from about 1.5 wt. % to about 6 wt. % hydroxyethyl starch or alternatively from about 2 wt. % to about 6 wt. % hydroxyethyl starch. The resultant compatibilized SAM (C-SAM) may be characterized by the formation of a coating of the compatibilizer on the particles of the SAM such that the coating covers greater than about 50% of the particle's surface; alternatively, greater than about 60%, 70%, 80% or 90% of the particle's surface.

In an embodiment, C-SAMs are introduced to the columns of apparatus 300. For example, the apparatus may be operated having sanitized SCP in column A (referring to FIG. 1A, column 310), a mixture of a sanitized SCP and a sanitized anionic exchange resin in column B (referring to FIG. 1, column 350) and a mixture of a SCP and a cationic exchange resin in column C (referring to FIG. 1, column 370). In an embodiment, the disclosed methodology comprises an extracorporeal device of the type depicted as apparatus 300 wherein bodily fluids (e.g., blood) obtained from a subject infected with a VISE (e.g., Ebola virus) or suspected of being infected with a VISE are contacted with the materials housed in the depicted columns in a sequence consisting essentially of contacting with a sanitized compatibilized SCP that is disposed within a first column (e.g., column A 310) to form a first filtrate that is introduced to a second column (e.g., column B 350) and contacted with a mixture of a sanitized compatibilized SCP and a sanitized compatibilized anion exchange resin to form a second filtrate. The second filtrate may subsequently introduced to a third column (e.g., column C 370) and contacted with a mixture of a sanitized compatibilized SCP and a sanitized compatibilized cation exchange resin to form a third filtrate. In an embodiment, a method of treating a subject infected with the VISE (e.g., Ebola virus) or suspected of being infected with the VISE (e.g., Ebola virus) comprises administering to the subject at least a portion of the third filtrate. In some embodiments, the third filtrate may be further processed by the addition of one or more agents that function to ameliorate the symptoms of the VISE.

In an embodiment, columns having both a sanitized, compatibilized SCP and a sanitized, compatibilized anion exchange resin disposed therein may have the ratio of sanitized compatibilized SCP to sanitized compatibilized anion exchange of from about 0.1:100 to about 100:0.1, alternatively from about 1:100 to about 100:1, or alternatively from about 10:100 to about 100:10, For example, columns having both a sanitized, compatibilized SCP and a sanitized, compatibilized anion exchange resin disposed therein may have the ratio of sanitized compatibilized SCP to sanitized compatibilized anion exchange of about 1:1, alternatively about 100:1, alternatively about 1:50, alternatively about 50:1, alternatively about 1:25, or alternatively about 25:1. In another embodiment, columns having both a sanitized, compatibilized SCP and a sanitized, compatibilized cation exchange resin disposed therein may have the ratio of sanitized compatibilized SCP to sanitized compatibilized cation exchange of from about 0.1:100 to about 100:0.1, alternatively from about 1:100 to about 100:1, or alternatively from about 10:100 to about 100:10, For example, columns having both a sanitized compatibilized SCP and a sanitized compatibilized cation exchange resin disposed therein may have the ratio of sanitized compatibilized SCP to sanitized compatibilized cation exchange resin range from of about 1:1, alternatively about 100:1, alternatively about 1:50, alternatively about 50:1, alternatively about 1:25, or alternatively about 25:1.

In an embodiment, columns having both a sanitized, compatibilized SCP and a sanitized, compatibilized anion exchange resin disposed therein may have the amount of sanitized compatibilized SCP to sanitized compatibilized anion exchange be from about 1 wt. % SCP to about 99 wt. % anion exchange resin based on the total dry weight of adsorbent materials, alternatively form about 10 wt. % SCP to about 90 wt. % anion exchange resin, alternatively from about 20 wt. % SCP to about 80 wt. % anion exchange resin, alternatively from about 30 wt. % SCP to about 70 wt. % anion exchange resin, alternatively from about 50 wt. % SCP to about 50 wt. % anion exchange resin, alternatively from about 75 wt. % SCP to about 25 wt. % anion exchange resin, alternatively from about 80 wt. % SCP to about 20 wt. % anion exchange resin, alternatively from about 90 wt. % SCP to about 10 wt. % anion exchange resin, or alternatively from about 99 wt. % SCP to about 1 wt. % anion exchange resin. In another embodiment, columns having both a sanitized compatibilized SCP and a sanitized compatibilized cation exchange resin disposed therein may have the amount of sanitized compatibilized SCP to sanitized compatibilized cation exchange resin be from about 1 wt. % SCP to 99 wt. % cation exchange resin based on the total weight of adsorbent materials, alternatively from about 10 wt. % SCP to about 90 wt. % cation exchange resin, alternatively from about 20 wt. % SCP to about 80 wt. % cation exchange resin, alternatively from about 30 wt. % SCP to about 70 wt. % cation exchange resin, alternatively from about 50 wt. % SCP to about 50 wt. % cation exchange resin, alternatively from about 75 wt. % SCP to about 25 wt. % cation exchange resin, alternatively from about 80 wt. % SCP to about 20 wt. % cation exchange resin, alternatively from about 90 wt. % SCP to about about 10 wt. % cation exchange resin, or alternatively from about 99 wt. % SCP to about 1 wt. % cation exchange resin.

In an embodiment, a subject suffering from a VISE or suspected of suffering from a VISE may be treated using the methodologies disclosed herein. For example, the subject may be placed in fluid communication with an extracorporeal apparatus of the type disclosed herein so as to allow bodily fluid (e.g., blood) of the subject to flow into an inlet port of the device. The extracorporeal apparatus may have columns situated in the apparatus to afford contact of the incoming bodily fluid with at least a first column having a sanitized SCP disposed therein to produce a first filtrate. The first filtrate may then be introduced to a second column having a mixture of a sanitized compatibilized SCP and a sanitized compatibilized anionic resin to produce a second filtrate. The second filtrate may be subsequently introduced to a third column comprising a sanitized compatibilized SCP and a sanitized compatibilized cationic resin to produce a third filtrate which may be returned to the subject.

In an embodiment, treatment of a subject suffering from a VISE or suspected of suffering from a VISE may result in a reduction in the level of disease mediators present in the bodily fluid (e.g., blood) of the subject. The presence of an elevated level of these disease mediators may result in hypercytokinemia where a number of pro-inflammatory cytokines and other pro-inflammatory substances are released by the immune cells within the body. A pro-inflammatory cytokine or a pro-inflammatory mediator is an immuno-regulatory cytokine that favors inflammation. Pro-inflammatory cytokines that are generally responsible for early immune responses include IL-1, IL-6, and TNFα. IL-1, IL-6, and TNF-α are also considered endogenous pyrogens as they contribute to increasing body temperature. Other examples of pro-inflammatory cytokines or pro-inflammatory mediators include IL-8, IL-4, L-11, IL-12, IL-18, GM-CSF, IFN-γ, TGF-β leukemia, inhibitory factors (LIF), oncostatin M (OSM), and a variety of chemokines that attract inflammatory cells.

A pro-inflammatory cytokine generally up-regulates or increases the synthesis of secondary pro-inflammatory mediators and other pro-inflammatory cytokines by immune cells. In addition, pro-inflammatory cytokines can stimulate production of acute phase proteins that mediate inflammation and attract inflammatory cells. IL-1 is an example of a pro-inflammatory cytokine. IL-1 is a soluble protein having a mass of approximately 17 kilo-Daltons (kD). IL-1 is produced by a variety of cells, for example macrophages, white blood cells, lymphocytes, monocytes, dendritic cells, and accessory cells that are involved in activation of T-lymphocytes and B-lymphocytes. IL-1 is typically released by such cells during an immune response. IL-1 is generally considered to be a pro-inflammatory cytokine. Pro-inflammatory cytokines generally refer to immunoregulatory cytokines that favor inflammation.

The original members of the IL-1 superfamily are interleukin-1 alpha (IL-1α), interleukin-1 beta (IL-β), and interleukin-1 receptor antagonist (IL-1RA) Both IL-1α and IL-1β play important roles in the inflammatory response of the body against pathogens or infection. Both IL-1α and IL-1β recognize a same IL-1 receptor and perform similar biological functions. IL-1α is predominantly a cell-associated molecule whereas IL-β is generally a secreted molecule.

IL-1 is produced during immune responses. A common function of IL-1 (e.g. IL-1α and IL-1β) is an increasing of expression of adhesion factors on endothelial cells to enable transmigration of leukocytes (which are immune cells that fight pathogens) to sites of infection. In addition, IL-1 stimulates the hypothalamus thermoregulatory center to cause an increase in body temperature (i.e. a fever). The increased body temperature helps the body's immune system to fight pathogens or infection within the body.

TNF-α is also an important pro-inflammatory cytokine. TNF-α is involved in systemic inflammation and works in tandem with a variety of other cytokines to stimulate the acute phase immune reaction. TNF-α is capable of inducing apoptotic cell death, induce inflammation, as well as inhibit tumorigenesis and viral replication. TNF-α and IL-1 commonly works simultaneously and synergistically in stimulating and sustaining inflammation within the body.

In an embodiment, the methods disclosed herein comprise extracorporeal exposure of the blood of the subjects in need thereof, to sanitized compatibilized adsorbent materials for a time sufficient to reduce the level of VISE-related disease mediators to less than about 50% of the amount present in the untreated bodily fluid, alternatively less than about 75%, or alternatively less than about 95%. For example the present methodologies may be effective in the removal from a bodily fluid (e.g., blood) of one or more substances associated with suppression of the subject's immune system (e.g., IL-18, IFN-γ, TNF-α, IL-1β), systemic inflammatory response syndrome (SIRS), (e.g., TNF-α, IL-1β, IL-6, IL-10, MCP-1, MCSF, MIP-1α), hypotension (e.g., NO) that leads to MOF, and compromise of vascular integrity (e.g., C3a, C5a, histamine) causing internal and external bleeding. Additional disease mediators are presented throughout the examples of the present disclosure.

TABLE 1

| Name | Also Known As | Designated |
| --- | --- | --- |
| Interleukin 18 | Interferon-gamma inducing factor | IL-18 |
| Interferon gamma | | IFN-γ |

TABLE 1-continued

| Name | Also Known As | Designated |
| --- | --- | --- |
| Tumor necrosis factor alpha | Cachexin, cachectin | TNF-α |
| Interleukin 6 | placental protein 12 (PP12) | IL-6 |
| Interleukin-1 beta | | IL1-β |
| Interleukin 10 | Human cytokine synthesis inhibitory factor (CSIF) | IL-10 |
| Monocyte chemotactic protein 1 | Chemokine (C-C motif) ligand 2 (CCL2) Small inducible cytokine A2 | MCP-1 |
| macrophage colony stimulating factor | colony stimulating factor 1 (CSF1) | M-CSF |
| Macrophage inflammatory protein | Chemokine (C-C) motif ligand 3 (CCL3) | MIP1α |
| Nitric oxide | | NO |
| C3a | Formed by cleavage of complement component 3 | |
| C5a | Formed by cleavage of complement component C5 | |
| histamine | 2-(1H-imidazol-4-yl)ethanamine | |

The effect of treatment of a VISE in terms of progression of the disease state may be monitored by any suitable methodology. For example, the level and amounts of one or more of the disclosed disease mediators (e.g., Table 1) in the blood of infected individuals may be determined and monitored during the course of treatment with the methodologies disclosed herein. In some embodiments, removal of VISE disease mediators may be determined by immunological methods such as enzyme-linked immunoassay (ELISA) and spectrophotometry, or combination thereof. The subject's improvement may also be evaluated clinically utilizing metrics such as but not limited to body temperature, hemodynamic parameters (blood pressure, pulse pressure, EKG) and general signs of improvement. For example, the compositions and methodologies disclosed herein may result in the reduction or inhibition the SIRS that develops due to the production of a "cytokine storm." Reduction or inhibition of the SIRS may be assessed by determination of the level of C-Reactive Protein (CRP) in the subject. In another embodiment, the compositions and methodologies disclosed herein may result in the improvement in VISE-associated hypotension. In another embodiment the compositions and methodologies disclosed herein may result in the improvement of the general health status of the VISE-infected subject as assessed by measurements of organ function such as but not limited to respiratory function, kidney function, and liver function. In another embodiment, the compositions and methodologies disclosed herein may result in the improvement of the immunological functioning of the VISE-infected subject as assessed by standard immunofunction assays such as a complete blood cell count with differential. In another embodiment, the compositions and methodologies disclosed herein may result in the improvement of the general health of the VISE-infected subject as assessed by decreases in the morbidity of a subject population and increased incidence of subject survival.

The present disclosure contemplates focusing on the pathophysiology of VISE infection allows deploying effective methods of treatment. This disclosure relates generally to extracorporeal cleansing of blood of a subject with a VISE. More specifically, it relates to the removal of VISE-associated disease mediators, permitting an infected subject to recover by regaining immune system capacity against the virus.

EXAMPLES

The subject matter of the present disclosure having been generally described, the following examples are given as particular embodiments of the disclosure and to demonstrate the practice and advantages thereof. It is understood that the examples are given by way of illustration and are not intended to limit the specification or the claims to follow in any manner.

Example One

Removal of EVD-Related Mediators by Mesorporous/Microporous Synthetic Carbon Beads from Human Fresh Frozen Plasma.

Two different synthetic carbon bead materials: -Carbon S-250/500TE7/20-4W-40C and -Carbon S-125/250-TE7/20-4W-50C were equilibrated prior to testing, and evaluated for the removal of a range of target molecules from certified human fresh frozen plasma (FFP). Prior to treatment, FFP (Lot No. 9247350, Sera Care Life Sciences, Milford, Mass.) was spiked with human cytokines (QIAGEN, Inc., Valencia, Calif.) at the following concentrations (pg/mL): TNF-α (100-225); IL-1 beta (70-110); IL-6 (80-115); IL-8 (225-475); IL-10 (85-125); TGF-beta 1 (450-1,450); INF-gamma (130-520); MCP-1 (120-160); and CRP (10-15 mg/L). Materials were incubated at 37° C. while mixing. At 0, 1, 2 and 4 hours intervals, samples were collected and analyzed. For endotoxin, nitric oxide (NO=$NO_2$— plus $NO_3$—), and hydrogen peroxide ($H_2O_2$), an additional series of experiments were carried out. Endotoxin, $NO_2$ and $NO_3$, and $H_2O_2$ were applied in concentrations of 0.777±0.082 EU/ml, 30.18±2.96 μM, 238.74±34.86 μM, and 7.76±0.9 nM, respectively. Controls consisted of spiked FFP only, with no adsorbent present. Materials were incubated at 37° C. while mixing (45 deg., 60 cycles/min, Aliquot Mixer, Model 4561, Ames Company, Ames, Iowa). Samples were collected at intervals as described above.

Cytokines/chemokines (TNF-α, IL-1 beta, IL-6, IL-8, IL-10, INF-gamma, MCP-1) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO concentrations after ethyl were established with the Cayman Chemical Nitrate/Nitrite Assay Kit (Cat. No. 780001, Ann Arbor, Mich.). Endotoxins (LPS) were evaluated with QCL-1000 Limulus Amebocyte Lysate Assay Kit (Product No. 50-647U, BioWhittaker, Walkersville, Md.). CRP was estimated using the commercial diagnostic kit from SIGMA Diagnostics (Procedure No. 371-A, St. Louis, Mo.). $H_2O_2$ was detected by spectrophotometry. The obtained results were tabulated, graphically expressed and analyzed.

The results of target molecules clearances are presented in FIGS. 2A-H which depict the effects of mesorporous/microporous synthetic carbon 250 or 125 on plasma clearances of: A: TNF-alpha; B: IL-beta; C: IL-6; D: IL-8; E: IL-10; F: MCP-1; G: IFN-gamma; and H: CRP and FIGS. 3A-D which depict the effects of mesorporous/microporous synthetic carbon 250 or 125 on plasma clearances of: A: nitrite; B: nitrate; C: endotoxin; and D: hydrogen peroxide.

The results demonstrate that synthetic carbons acted non-specifically in removing EVD target molecules based on their molecular mass. Both carbons, 250 and 125, effectively cleared all small inorganic and organic molecules. Synthetic carbon 250 was more specific toward larger peptides/proteins (ie, TNF-alpha) and carbon 125 toward smaller ones.

Example Two

Removal of EVD-Related Mediators by Anion Exchange Resin from Human Fresh Frozen Plasma.

UNOsphere Q Media (Bio-Rad, Hercules, Calif.), was equilibrated prior to testing, and evaluated for the removal of a range of target molecules from certified human fresh frozen plasma (FFP). Prior to treatment, FFP (Lot No. 9247350, Sera Care Life Sciences, Millford, Mass.) was spiked with human cytokines (QIAGEN, Inc., Valencia, Calif.) at the following concentrations (pg/mL): TNF-α (100-225); IL-1 beta (70-110); IL-8 (225-475); IL-10 (85-125); TGF-beta 1 (450-1,450); IL-6 (80-115); INF-gamma (130-520); IL-12 (85-120); MCP-1 (120-160); MIP-1 alpha (80-120). Materials were incubated at 37° C. while mixing. At 0, 1, 2 and 4 hours intervals, samples were collected and analyzed for specific cytokine levels. For endotoxin, NO ($NO_2$—/$NO_3$—) and hydrogen peroxide ($H_2O_2$) an additional series of experiments was carried out. Endotoxin, $NO_2$, $NO_3$, and $H_2O_2$ were applied in concentrations of 0.777±0.082 EU/ml, 30.18±2.96 μM, 238.74±34.86 μM, and 18.5±3.0, respectively. Controls consisted of spiked FFP only, with no adsorbent present. Materials were incubated at 37° C. while mixing (45 deg, 60 cycles/min, Aliquot Mixer, Model 4561, Ames Company, Ames, Iowa). Samples were collected at intervals as described for cytokines and analyzed.

Cytokines/chemokines (TNF-α, IL-1 beta, IL-8, IL-10, TGF-beta 1, IL-6, INF-gamma, IL-12, MCP-1, MIP-1 alpha) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO concentrations after ethyl were established with the Cayman Chemical Nitrate/Nitrite Assay Kit (Cat. No. 780001, Ann Arbor, Mich.). Endotoxins (LPS) were evaluated with QCL-1000 Limulus Amebocyte Lysate Assay Kit (Product No. 50-647U, BioWhittaker, Walkersville, Md.). $H_2O_2$ was measured using spectrophometric method.

The results of target molecules clearances are presented in FIGS. 3A, B, C, D, E & F which correspond to clearances of: A: TNF-alpha, IL-1 beta, IL-6; B: IL-8; C: IL-10, MCP-1, MIP-1; D: TGF-beta 1, INF-gamma; E: Nitrite, Nitrate, Hydrogen peroxide; and F: Endotoxin, respectively.

The performed analyses demonstrate that Q Media removed a substantial amount of EVD disease mediators. Q Media had positive effects on peptide-, protein-based inflammatory mediators and small molecules that are electronegative in charge at physiologic pH.

Example Three

Removal of EVD-Related Mediators by Cation Exchange Resin from Human Fresh Frozen Plasma.

UNOsphere S Media (Bio-Rad, Hercules, Calif.), was equilibrated prior to testing, and evaluated for the removal of a range of target molecules from certified human fresh frozen plasma (FFP). Prior to treatment, FFP (Lot No. 9247350, Sera Care Life Sciences, Millford, Mass.) was spiked with human cytokines (QIAGEN, Inc., Valencia, Calif.) at the concentrations provided in TABLE 2 with: TNF-α; IL-1 beta; IL-2; IL-6; IL-10; TGF-beta 1; INF-gamma; and IL-4. Materials were incubated at 37° C. while mixing. At 0, 1, 2 and 4 hours intervals, samples were collected and analyzed for specific cytokine levels. For endotoxin and NO, an additional series of experiments were carried out. Controls consisted of spiked FFP only, with no adsorbent present. Materials were incubated at 37° C. while mixing (45 deg., 60 cycles/min, Aliquot Mixer, Model 4561, Ames Company, Ames, Iowa). Samples were collected at intervals as described for cytokines and analyzed.

Cytokines/chemokines (TNF-α, IL-1 beta, IL-2, IL-4, IL-6 IL-10, TGF-beta 1, INF-gamma) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). NO concentrations were established with the Cayman Chemical Nitrate/Nitrite Assay Kit (Cat. No. 780001, Ann Arbor, Mich.). Endotoxins (LPS) were evaluated with QCL-1000 Limulus Amebocyte Lysate Assay Kit (Product No. 50-647U, BioWhittaker, Walkersville, Md.).

The results of target molecules clearances are presented in TABLE 2. The results demonstrate that S Media showed the cationic exchange properties, targeting molecules that are electropositively charged under the physiological pH. The cationic inflammatory cytokines such as TGF-beta 1, IL-4 and IFN-gamma were effectively cleared. This chromatographic resin did not react with albumin, endotoxin and NO.

TABLE 2

| # | analyte | time (hr) | run # 1 | change (%) | sorbing per gram of dewatered S Media | run # 2 | change (%) | sorbing per gram of dewatered S Media |
|---|---|---|---|---|---|---|---|---|
| 1 | NO3 (umol) | 0 | 59.65 | | | 59.65 | | |
|  | 65.01 umol | 1 | 64.2 | (−) 7.63 | N/A | 56.23 | 5.73 | 48.84 umol |
|  |  | 4 | 56.81 | 4.81 | 40.56 umol | 63.63 | (−) 6.67 | N/A |
| 2 | endotoxin (EU/mL) | 0 | 0.243 | | | 0.277 | | |
|  | 0.27 EU/mL | 1 | 0.151 | 37.86 | 1.31 EU | 0.198 | 28.52 | 1.13 EU |
|  |  | 4 | 0.185 | 23.87 | 0.83 EU | 0.151 | 45.49 | 1.80 EU |
| 3 | TGF beta 1 (ng/mL) cationic molecule | 0 | 2.45 | | | 2.32 | | |
|  | 2.50 ng/mL | 1 | 0.06 | 97.55 | 34.13 ng | 0.07 | 96.98 | 32.13 ng |
|  |  | 4 | 0.05 | 97.96 | 34.99 ng | 0.06 | 97.41 | 32.27 ng |
| 4 | IL-1 beta (pg/mL) neutral molecule | 0 | 27.72 | | | 28.5 | | |
|  | 30.5 pg/mL | 1 | 29.1 | (−) 4.98 | N/A | 29.95 | (−) 5.09 | N/A |
|  |  | 4 | 25.89 | 6.6 | 26.13 pg | 32.43 | (−) 13.79 | N/A |
| 5 | IL-2 (pg/mL) neutral molecule | 0 | 403.15 | | | 387.59 | | |
|  | 435.7 pg/mL | 1 | 423.89 | (−) 10.89 | N/A | 347.41 | 10.37 | 573.77 pg |
|  |  | 4 | 434.26 | (−) 7.72 | N/A | 383.7 | 1 | 55.55 pg |
| 6 | IL-4 (pg/mL) cationic molecule | 0 | 360.99 | | | 365.11 | | |
|  | 375.07 pg/mL | 1 | 222.48 | 38.37 | 1,977.92 pg | 187.86 | 48.55 | 2,531.99 pg |
|  |  | 4 | 151.71 | 57.97 | 4,930.74 pg | 163.18 | 55.31 | 2,883.56 pg |
| 7 | IFN gamma (pg/mL) cationic molecule | 0 | 301.11 | | | 326.5 | | |
|  | 325.8 pg/mL | 1 | 198.06 | 34.22 | 1,471.55 pg | 164.8 | 49.53 | 2,309.08 pg |
|  |  | 4 | 101.4 | 66.32 | 2,851.56 pg | 123.51 | 62.17 | 2,898.70 pg |
| 8 | IL-6 (pg/mL) anionic molecule | 0 | 308.14 | | | 284.46 | | |

TABLE 2-continued

| # | analyte | time (hr) | run #1 | change (%) | sorbing per gram of de-watered S Media | run #2 | change (%) | sorbing per gram of de-watered S Media |
|---|---------|-----------|--------|------------|-----------------------------------------|--------|------------|-----------------------------------------|
|   | 350.72 pg/mL | 1 | 359.79 | (−) 16.76 | N/A | 343.26 | (−) 20.67 | N/A |
|   |         | 4 | 300.99 | 2.32 | 102.10 pg | 297.49 | (−) 4.58 | N/A |
| 9 | IL-10 (pg/mL) anionic molecule | 0 | 424.08 | | | 480 | | |
|   | 475.1 pg/mL | 1 | 419.26 | 1.14 | 68.83 pg | 464.96 | (−) 3.13 | N/A |
|   |         | 4 | 411.26 | 3.02 | 183.07 pg | 489.37 | (−) 1.95 | N/A |
| 10 | albumin (g/dL) | 0 | 3.4 | | | 3.4 | | |
|   | 3.5 g/dL | 1 | 3.2 | 5.88 | 2.86 g | 3.1 | 8.82 | 4.28 g |
|   |         | 4 | 3 | 11.76 | 5.71 g | 3 | 11.76 | 5.71 g |

Example Four

Removal of EVD-Related Mediators by Mesorporous/Microporous Synthetic Carbon Beads from Human Whole Blood.

Two formulations of mesoporous/microporous synthetic carbon (125/250 & 250/500) were brought to pharmaceutical grade using validated sanitization and fine particulates removal methods. Then mesoporous/microporous synthetic carbon beads were used in the agitation testing protocol identical to that described in Examples 1-3, or packed into adsorbing devices in sizes representing a 36× scale down from the average human extracorporeal circuit (ECMO) model. Prior to testing, the carbon beads were treated/coated with a solution containing 1% dextran in 09% NaCl, USP (NDC 0409-7419-03, Hospira, Lake Forest, Ill.) and 3,000U HMW heparin (Heparin, Sodium Injection, USP, 1000 U/mL, NDC 0641-2440-41 6505-00-153-9740, Elkins-Sinn, Inc., Cherry Hill, N.J.), and later in the agitation experiment combined with 15 mL of spiked fresh human blood or in extracorporeal experiment filled with 76 mL of spiked fresh human whole blood, warmed to 37° C. Before spiking, human whole blood was filtered using 20 μm Pall filter, which was disconnected during testing. In the extracorporeal experiment, the back-pressure determined the flow rate generated by a peristaltic pump. In both experiments, sampling occurred at 0, 1, and 4 hours. In the agitation experiments tubes containing carbon beads were mixed horizontally, and in the extracorporeal experiments the cartridges containing carbon adsorbents were oriented vertically. In both experiments done in duplicates, human whole blood was spiked with inflammatory cytokines (TNF-α, IL-1β, IL-4. IL-6, IL-8, IL-10, IFN-gγ, TGF-β1), endotoxin, NO, and $H_2O_2$ thereby, mimicking EVD state.

Cytokines/chemokines (TNF-α, IL-1β, IL-4, IL-6, IL-8, IL-10, TGF-β1, IFN-γ) were evaluated by the Multi-Analyte Custom ELISArray Kit (CELISA-CMEH0400A, QIAGEN Inc., Valencia, Calif.). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, Calif.) and calculated using Microplate Manager Software Version 2.2 (Bio-Rad Laboratories). $NO_2/NO_3$=NO concentrations after ethyl were established with the Cayman Chemical Nitrate/Nitrite Assay Kit (Cat. No. 780001, Ann Arbor, Mich.). Endotoxins (LPS) were evaluated with QCL-1000 Limulus Amebocyte Lysate Assay Kit (Product No. 50-647U, BioWhittaker, Walkersville, Md.). CRP was estimated using the commercial diagnostic kit from SIGMA Diagnostics (Procedure No. 371-A, St. Louis, Mo.). Hydrogen peroxide was assayed spectrophotometrically. The results of target molecule clearances are presented in TABLES 3-14 for extracorporeal testing and TABLES 3A-14A for agitation testing.

The results demonstrate that mesoporous/microporous synthetic carbon beads were effective in removal of EVD mediators responsible for SIRS, immune system suppression, hypotension and MOF. Synthetic carbon beads in experimental conditions investigated, extracorporeal and agitation, showed similar cleansing effectiveness toward EVD mediators.

TABLE 3

INTERFEREON GAMMA

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 87.31 | 6,635 | — | 0 | — | — | — |
| 1 | 25.29 | 1,922 | 589.1 | 1 | — | — | — |
| 4 | 27.69 | 2,105 | 566.2 | 4 | — | — | — |

TABLE 3A

INTERFEREON GAMMA

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 86.70 | 1,300.5 | — | 0 | — | — | — |
| 1 | 28.90 | 433.5 | 548.7 | 1 | — | — | — |
| 4 | 28.9 | 433.5 | 548.7 | 4 | — | — | — |

TABLE 4

C-reactive protein

| | RUN 1 | | | RUN 2 | |
|---|---|---|---|---|---|
| Time (hr) | mg/dL whole blood | % decrease | Time (hr) | mg/dL whole blood | % decrease |
| 0 | 2.01 | — | 0 | — | — |
| 1 | 0.157 | 92.2 | 1 | — | — |
| 4 | 0.377- | 81.2 | 4 | — | — |

TABLE 4A

C-reactive protein

| | RUN 1 | | | RUN 2 | |
|---|---|---|---|---|---|
| Time (hr) | mg/dL whole blood | % decrease | Time (hr) | mg/dL whole blood | % decrease |
| 0 | 2.29 | — | 0 | — | — |
| 1 | 0.472 | 79.4 | 1 | — | — |
| 4 | 0.251 | 89.03 | 4 | — | — |

TABLE 5

ENDOTOXIN

| | RUN 1 | | | | RUN 2 | |
|---|---|---|---|---|---|---|
| Time (hr) | EU/mL whole blood | EU/ 76 mL whole blood | EU per g sorbent | Time (hr) | EU/mL whole blood | EU/ 76 mL whole blood | EU per g sorbent |
| 0 | 0.747 | 58.82 | — | 0 | 0.755 | 57.38 | — |
| 1 | 0.205 | 15.58 | 5.405 | 1 | 0.190 | 14.47 | 5.364 |
| 4 | 0.178 | 13.53 | 5.661 | 4 | 0.175 | 13.32 | 5.507 |

TABLE 5A

ENDOTOXIN

| | RUN 1 | | | | RUN 2 | | |
|---|---|---|---|---|---|---|---|
| Time (hr) | EU/mL whole blood | EU/ 15 mL whole blood | EU per g sorbent | Time (hr) | EU/mL whole blood | EU/ 15 mL whole blood | EU per g sorbent |
| 0 | 0.831 | 12.46 | — | 0 | 0.757 | 11.359 | — |
| 1 | 0.262 | 3.926 | 5.401 | 1 | 0.228 | 3.426 | 4.989 |
| 4 | 0.102 | 1.537 | 6.913 | 4 | 0.173 | 3.595 | 5.547 |

TABLE 6

TGF-β1

| | RUN 1 | | | | RUN 2 | | |
|---|---|---|---|---|---|---|---|
| Time (hr) | pg/mL whole blood | pg/ 76 mL whole blood | pg per g sorbent | Time (hr) | pg/mL whole blood | pg/ 76 mL whole blood | pg per g sorbent |
| 0 | 1,303.5 | 99,066 | — | 0 | 1,291 | 98,116 | — |
| 1 | 1,149.3 | 87,346 | 1,465 | 1 | 1,081 | 82,156 | 1,995 |
| 4 | 778.95 | 59,200 | 4,983 | 4 | 738.1 | 56,095 | 5,252 |

TABLE 6A

TGF-β1

| | RUN 1 | | | | RUN 2 | | |
|---|---|---|---|---|---|---|---|
| Time (hr) | pg/mL whole blood | pg/ 15 mL whole blood | pg per g sorbent | Time (hr) | pg/mL whole blood | pg/15 mL whole blood | pg per g sorbent |
| 0 | 1,249 | 18,735 | — | 0 | 1,303 | 19,545 | — |
| 1 | 855 | 12.825 | 3,740 | 1 | 950.2 | 14,253 | 3,349 |
| 4 | 783 | 11,745 | 4,424 | 4 | 768.4 | 11,520 | 5,063 |

TABLE 7

TNF-α

| | RUN 1 | | | | RUN 2 | | |
|---|---|---|---|---|---|---|---|
| Time (hr) | pg/mL whole blood | pg/ 76 mL whole blood | pg per g sorbent | Time (hr) | pg/mL whole blood | pg/ 76 mL whole blood | pg per g sorbent |
| 0 | 1,898.9 | 144,323 | — | 0 | — | — | — |
| 1 | 1,506.2 | 114,469 | 3,731.7 | 1 | — | — | — |
| 4 | 825.4 | 62,735 | 10,198.7 | 4 | — | — | — |

TABLE 7A

TNF-α

| | RUN 1 | | | | RUN 2 | | |
|---|---|---|---|---|---|---|---|
| Time (hr) | pg/mL whole blood | pg/ 15 mL whole blood | pg per g sorbent | Time (hr) | pg/mL whole blood | pg/ 15 mL whole blood | pg per g sorbent |
| 0 | 2,007.1 | 30,106.5 | — | 0 | — | — | — |
| 1 | 1,614.3 | 24,214.5 | 3,729.1 | 1 | — | — | — |
| 4 | 681.5 | 10,222.8 | 12,584.6 | 4 | — | — | — |

TABLE 8

IL-4

| | RUN 1 | | | | RUN 2 | | |
|---|---|---|---|---|---|---|---|
| Time (hr) | pg/mL whole blood | pg/ 76 mL whole blood | pg per g sorbent | Time (hr) | pg/mL whole blood | pg/76 mL whole blood | pg per g sorbent |
| 0 | 54.29 | 4,125.8 | — | 0 | 40.83 | 3,103.16 | — |
| 1 | 48.99 | 3,723.8 | 50.25 | 1 | 37.54 | 2,853.04 | 31.26 |
| 4 | 38.69 | 2,940.7 | 148.1 | 4 | 32.92 | 2,501.84 | 75.16 |

TABLE 8A

IL-4

| | RUN 1 | | | | RUN 2 | |
|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 71.03 | 1,065.5 | — | 0 | 76.23 | 1,143.4 | — |
| 1 | 66.41 | 996.23 | 43.84 | 1 | 76.23 | 1,143.4 | 0 |
| 4 | 62.37 | 935.59 | 82.22 | 4 | 62.37 | 935.59 | 131.52 |

TABLE 9

IL-6

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 5,467.8 | 415,550 | — | 0 | 4,619.4 | 351,080 | — |
| 1 | 2,835.5 | 215,500 | 25,006 | 1 | 3,308.1 | 251,420 | 12,450 |
| 4 | 1,473.9 | 112,020 | 37,941 | 4 | 1,551.4 | 117,910 | 29,150 |

TABLE 10

IL-8

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 2,139 | 162,576 | — | 0 | 2,366 | 179,845 | — |
| 1 | 1,816 | 138,036 | 3,067.5 | 1 | 1,728.1 | 131,333 | 6,064 |
| 4 | 1,388 | 105,540 | 7,129.5 | 4 | 1,367.8 | 103,953 | 9,486 |

TABLE 9A

IL-6

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 4,958.5 | 74,378 | — | 0 | 4,673 | 70,105 | — |
| 1 | 1,944.6 | 29,169 | 28,610 | 1 | 1,696 | 25,450 | 28,260 |
| 4 | 999.4 | 14,991 | 37,590 | 4 | 859 | 12,899 | 36,210 |

TABLE 10A

IL-8

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 1,955.3 | 29,329 | — | 0 | 2,054 | 30,809 | — |
| 1 | 1,204.8 | 18,072 | 7,125 | 1 | 1,432 | 21,481 | 5,904 |
| 4 | 837.1 | 12,556 | 10,615 | 4 | 734 | 11,010 | 12,531 |

TABLE 11

IL-10

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 3,004 | 228,304 | — | 0 | 2,381.8 | 181,017 | — |
| 1 | 997 | 75,772 | 19,066 | 1 | 675.7 | 51,353 | 16,208 |
| 4 | 343.8 | 26,129 | 25,272 | 4 | 169.5 | 12.882 | 21,017 |

TABLE 11A

IL-10

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 3,214 | 48,210 | — | 0 | 3,240 | 48,600 | — |
| 1 | 1,767.6 | 26,514 | 13,732 | 1 | 1,751.1 | 26,266 | 14,135 |
| 4 | 723.2 | 10,848 | 23,647 | 4 | 621.2 | 9,318 | 24,862 |

TABLE 12

IL-1β

| | RUN 1 | | | | RUN 2 | | |
|---|---|---|---|---|---|---|---|
| Time (hr) | pg/mL whole blood | pg/76 mL whole blood | pg per g sorbent | Time (hr) | pg/mL whole blood | pg/76 mL whole blood | pg per g sorbent |
| 0 | 154.52 | 11,743.5 | — | 0 | 150.65 | 11,449 | — |
| 1 | 84.98 | 6,458.5 | 660 | 1 | 88.84 | 6,752 | 587.1 |
| 4 | 0 | 0 | 1,467.9 | 4 | 0 | 0 | 1,431.1 |

TABLE 12A

IL-1β

| | RUN 1 | | | | RUN 2 | | |
|---|---|---|---|---|---|---|---|
| Time (hr) | pg/mL whole blood | pg/15 mL whole blood | pg per g sorbent | Time (hr) | pg/mL whole blood | pg/15 mL whole blood | pg per g sorbent |
| 0 | 118.98 | 1,784.7 | — | 0 | 122.06 | 1,831.02 | — |
| 1 | 42.58 | 638.71 | 725 | 1 | 50.75 | 761.20 | 677.1 |
| 4 | 7.72 | 115.8 | 1,056.2 | 4 | 4.63 | 69.53 | 1,114.8 |

TABLE 13

Nitric Oxide (NO = $NO_2 + NO_3$)

| | RUN 1 | | | RUN 2 | |
|---|---|---|---|---|---|
| Time (hr) | uM whole blood | % decrease | Time (hr) | uM whole blood | % decrease |
| 0 | 255.4 | — | 0 | — | — |
| 1 | 0.501 | 95.0 | 1 | — | — |
| 4 | 0.000- | 100 | 4 | — | — |

TABLE 13A

Nitric Oxide (NO = $NO_2 + NO_3$)

| | RUN 1 | | | RUN 2 | |
|---|---|---|---|---|---|
| Time (hr) | uM whole blood | % decrease | Time (hr) | uM whole blood | % decrease |
| 0 | 252.3 | — | 0 | — | — |
| 1 | 100.9 | 60.0 | 1 | — | — |
| 4 | 35.7 | 85.8 | 4 | — | — |

TABLE 14

Hydrogen Peroxide ($H_2O_2$)

| | RUN 1 | | | RUN 2 | |
|---|---|---|---|---|---|
| Time (hr) | nM whole blood | % decrease | Time (hr) | nM whole blood | % decrease |
| 0 | 235.7 | — | 0 | — | — |
| 1 | 85.8 | 63.6 | 1 | — | — |
| 4 | 27.9 | 88.2 | 4 | — | — |

TABLE 14A

Hydrogen Peroxide ($H_2O_2$)

| | RUN 1 | | | RUN 2 | |
|---|---|---|---|---|---|
| Time (hr) | nM whole blood | % decrease | Time (hr) | nM whole blood | % decrease |
| 0 | 9.70 | — | 0 | — | — |
| 1 | 0.157 | 92.2 | 1 | — | — |
| 4 | 0.000- | 100 | 4 | — | — |

Example Five

Effect of Sanitization of Mesoporus/Microporous Synthetic Carbon Beads (125 & 250), Q Media and S Media on Their Sorbing Capacity Toward EVD-Related Mediators and Physiologic Parameters.

De-watered mesoporous/microporous Synthetic Carbon Beads 125 and 250, Q Media and S Media (in weight proportions: 50%. 20%. 20%, 10%, respectively) in non-sterile (industrial grade) and sterile (pharmaceutical grade) forms, were packed in a Bio-Rad chromatography column (ID 65 mm×17 mm) and tested for the removal of the target molecules in the EVD condition. After packing, the chromatographic material was primed with 1% LMW Dextran 40 in 0.9% NaCl, USP (NDC 0409-7419-03, Hospira). Then the column was connected with the extracorporeal circuit filled with spiked FFP, as described in Example 4. FFP extracorporeal cleansing was conducted for 4 hours. Samples were collected at 0, 1 and 4 hrs and subjected for analyses, as described in previous Examples. Additionally, physiologic parameters were established using Abaxis Piccolo Xpress Chemistry Analyzer and IRMA TruPoint Blood Analysis System. Table 15 provides metrics regarding the adsorbent material's clearance for the indicated compound (parameter) before sanitization (Industrial Grade) while Table 16 provides metrics regarding the adsorbent material's clearance for the indicated compound after sanitization (Pharmaceutical Grade).

The results presented in Tables 15 and 16 demonstrate adsorbents formulations, which contained synthetic carbons 250 and 125, Q Media and S Media, not subjected for sanitization, very effectively removed mediators of EVD and the effect on physiological mediators was minimal. It was further noted that sanitization of adsorbents (synthetic carbons 250 and 125, Q Media and S Media), had almost no effect on their sorbing/binding potency toward EVD mediators.

TABLE 15

| PARAMETER | 0 HR | 1 HR | % CHANGE | 4 HR | % CHANGE |
|---|---|---|---|---|---|
| TNF alpha (pg/mL) | 759.59 | 282.81 | −62.8 | 183.37 | −75.8 |
| IL-1 beta (pg/mL) | 156.59 | 90.91 | −41.9 | 86.01 | −45.1 |
| IL-6 (pg/mL) | 325.20 | 92.63 | −71.5 | 61.32 | −81.1 |
| IL-8 (pg/mL) | 881.76 | 217.43 | −75.3 | 101.22 | −88.5 |
| IL-10 (pg/mL) | 934.45 | 393.62 | −57.9 | 218.72 | −76.6 |
| TGF beta 1 (pg/mL) | 1393.75 | 109.25 | −92.2 | 45.93 | −96.7 |
| endotoxin (EU/mL) | 1.036 | 0.131 | −87.3 | 0.149 | −85.6 |
| C3a des Arg (ng/mL) | 3192.2 | 1562.3 | −51.0 | 668.9 | −79.0 |
| nitric oxide (uM) | 95.39 | 48.70 | −48.9 | 58.54 | −38.6 |
| ALB (g/dL) | 4.4 | 4.1 | −6.8 | 3.9 | −11.4 |
| ALP (U/L) | 41 | 35 | −14.6 | 37 | −9.7 |
| ALT (U/L) | 15 | 8 | −46.7 | 6 | −60.0 |
| AMY (U/L) | 84 | 54 | −35.7 | 53 | −36.9 |
| TBIL (mg/dL) | 0.7 | 0.7 | 0 | 0.6 | −14.3 |
| BUN (mg/dL) | 12 | 10 | −16.7 | 11 | −8.3 |
| Ca (mg/dL) | 6.5 | 4.9 | −24.6 | 4.9 | −24.6 |
| PHOS (mg/dL) | 9.7 | 9.0 | −7.2 | 8.9 | −8.2 |
| CRE (mg/dL) | 0.9 | 0.2 | −77.8 | 0.3 | −66.7 |
| GLU (mg/dL) | 341 | 268 | −21.4 | 265 | −22.3 |
| Na+ (mM) | 157 | 150 | −4.4 | 146 | −7.0 |
| K+ (mM) | 3.7 | 3.4 | −8.1 | 3.3 | −10.8 |
| TP (g/dL) | 6.9 | 6.4 | −7.2 | 6.0 | −13.0 |
| GLOB (g/dL) | 2.5 | 2.3 | −8.0 | 2.1 | −16.0 |
| pH | 7.579 | 7.490 | 1.2 | | |

TABLE 16

| PARAMETER | 0 HR | 1 HR | % CHANGE | 4 HR | % CHANGE |
|---|---|---|---|---|---|
| TNF alpha (pg/mL) | 787.15 | 304.24 | −61.3 | 294.16 | −62.6 |
| IL-1 beta (pg/mL) | 162.51 | 80.28 | −50.6 | 103.52 | −36.3 |
| IL-6 (pg/mL) | 437.36 | 138.70 | −68.3 | 20.38 | −95.3 |
| IL-8 (pg/mL) | 952.76 | 225.82 | −76.3 | 104.81 | −89.0 |
| IL-10 (pg/mL) | 920.25 | 432.49 | −53.0 | 205.66 | −77.6 |
| TGF beta 1 (pg/mL) | 1402.45 | 163.66 | −88.3 | 157.58 | −88.8 |
| endotoxin (EU/mL) | 1.015 | 0.151 | −85.1 | 0.123 | −87.9 |
| C3a des Arg (ng/mL) | 3322.6 | 1808.5 | −45.6 | 330.2 | −90.1 |
| nitric oxide (uM) | 95.20 | 57.32 | −39.8 | 61.39 | −35.5 |
| ALB (g/dL) | 4.4 | 4.1 | −6.8 | 4.0 | −9.0 |
| ALP (U/L) | 40 | 37 | −7.5 | 31 | −22.5 |
| ALT (U/L) | 9 | 16 | 77.8 | 12 | −33.3 |
| AMY (U/L) | 62 | 55 | −11.3 | 53 | −14.5 |
| TBIL (mg/dL) | 0.6 | 0.6 | 0 | 0.6 | 0 |
| BUN (mg/dL) | 12 | 11 | −8.3 | 12 | 0 |
| Ca (mg/dL) | 6.6 | 5.0 | −24.2 | 5.0 | −24.2 |
| PHOS (mg/dL) | 9.6 | 9.2 | −4.2 | 8.8 | −8.3 |
| CRE (mg/dL) | 1.0 | 0.4 | −60.0 | 0.2 | −80.0 |
| GLU (mg/dL) | 347 | 264 | −76.0 | 266 | −23.3 |
| Na+ (mM) | 156 | 150 | −3.8 | 148 | −5.1 |
| K+ (mM) | 3.9 | 3.4 | −12.8 | 3.4 | −12.8 |
| TP (g/dL) | 7.1 | 6.4 | −9.8 | 6.4 | −9.8 |
| GLOB (g/dL) | 2.7 | 2.3 | −14.8 | 2.5 | −7.4 |
| pH | 7.586 | | | 7.549 | 0.5 |

Example Six

Impact of Priming/Coating of Mesoporous/Microporous Synthetic Carbons with LMW Dextran on their Sorbing Capacity Toward Small and Large Molecules.

Figure 4A:
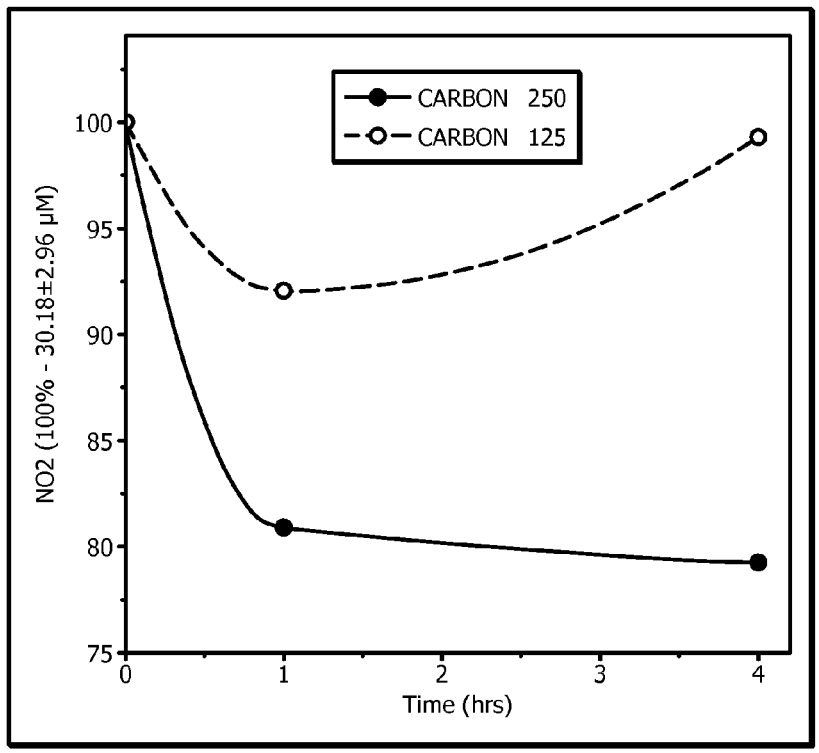
FIG. 4A is a plot of the amount of nitrite in a sample of fresh frozen plasma as a function of time following contact with the indicated adsorbent.
Figure 4B:
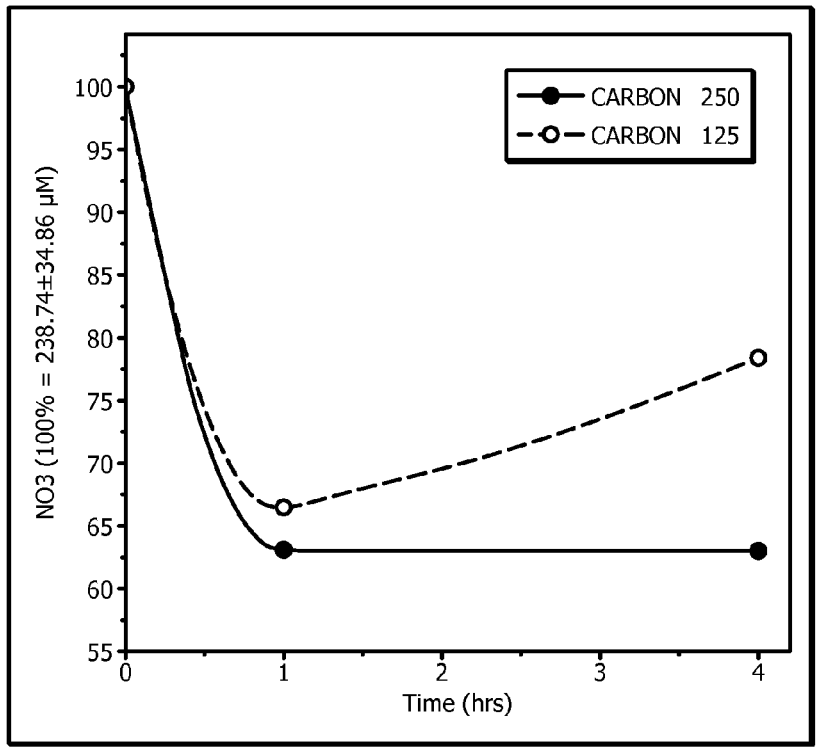
FIG. 4B is a plot of the amount of nitrate in a sample of fresh frozen plasma as a function of time following contact with the indicated adsorbent.
Figure 4C:
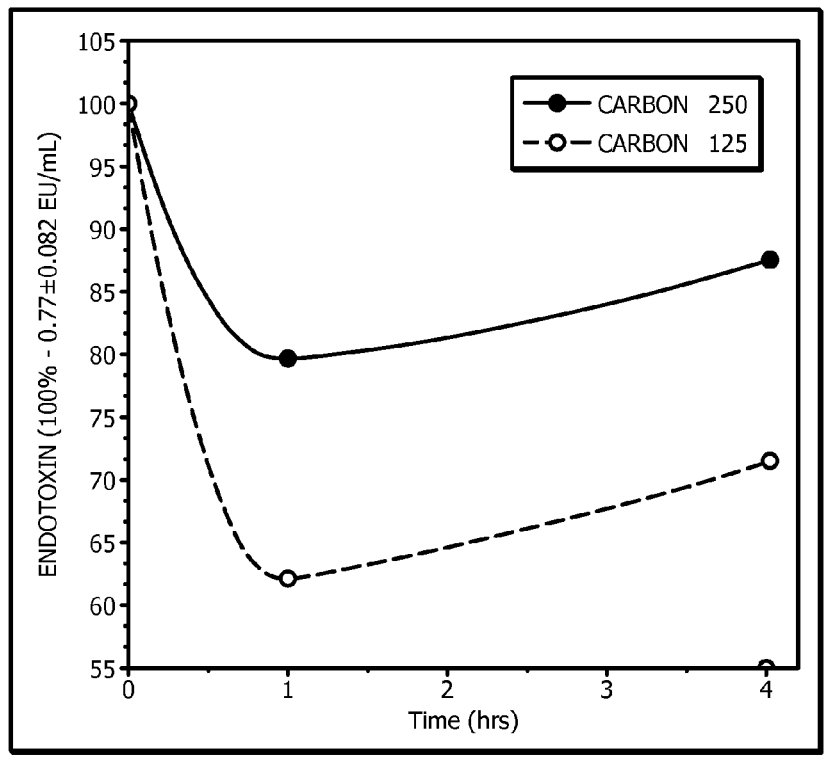
FIG. 4C is a plot of the amount of endotoxin in a sample of fresh frozen plasma as a function of time following contact with the indicated adsorbent.
Figure 4D:
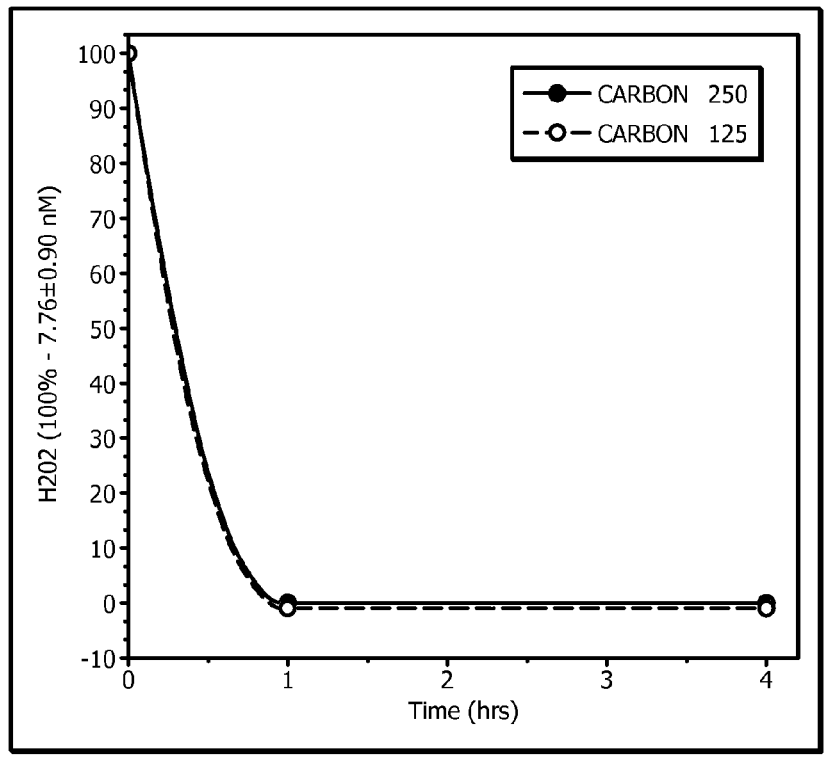
FIG. 4D is a plot of the amount of hydrogen peroxide in a sample of fresh frozen plasma as a function of time following contact with the indicated adsorbent.
Figure 5A:
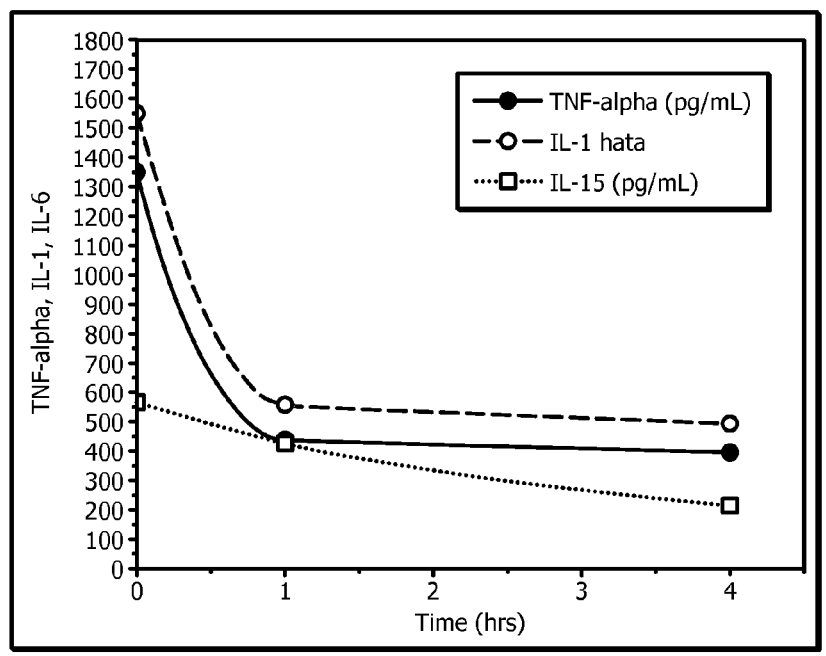
FIG. 5A is a plot of the amount of TNFα, IL-1β and IL-6 in a sample of whole blood as a function of time following contact with the indicated adsorbent.
Figure 5B:
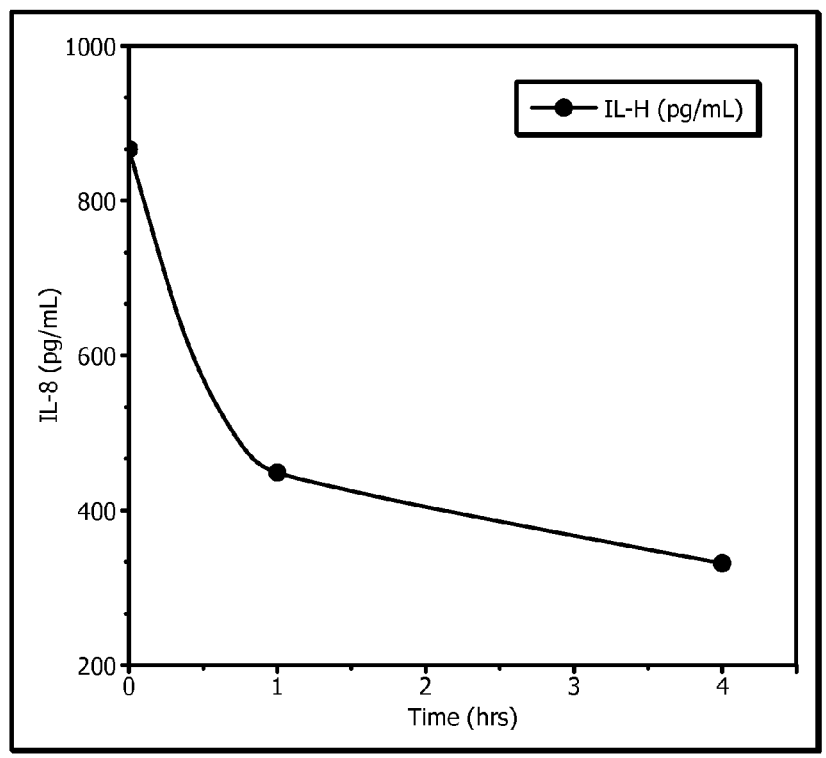
FIG. 5B is a plot of the amount of IL-8 in a sample of fresh frozen plasma as a function of time following contact with the indicated adsorbent.
Figure 5C:
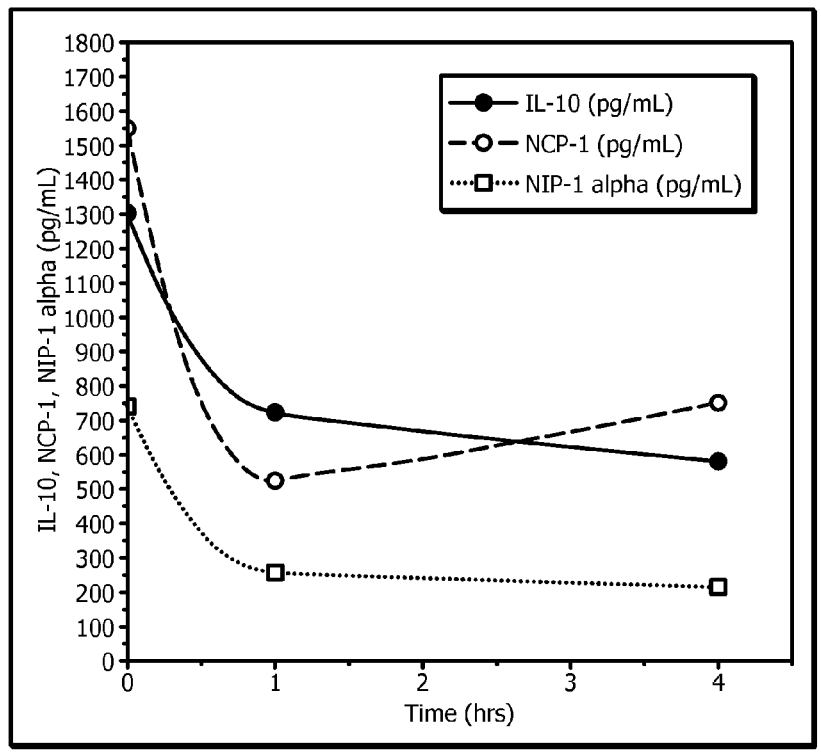
FIG. 5C is a plot of the amount of IL-10, MCP-1 and MCP1α in a sample of fresh frozen plasma as a function of time following contact with the indicated adsorbent.
Figure 5D:
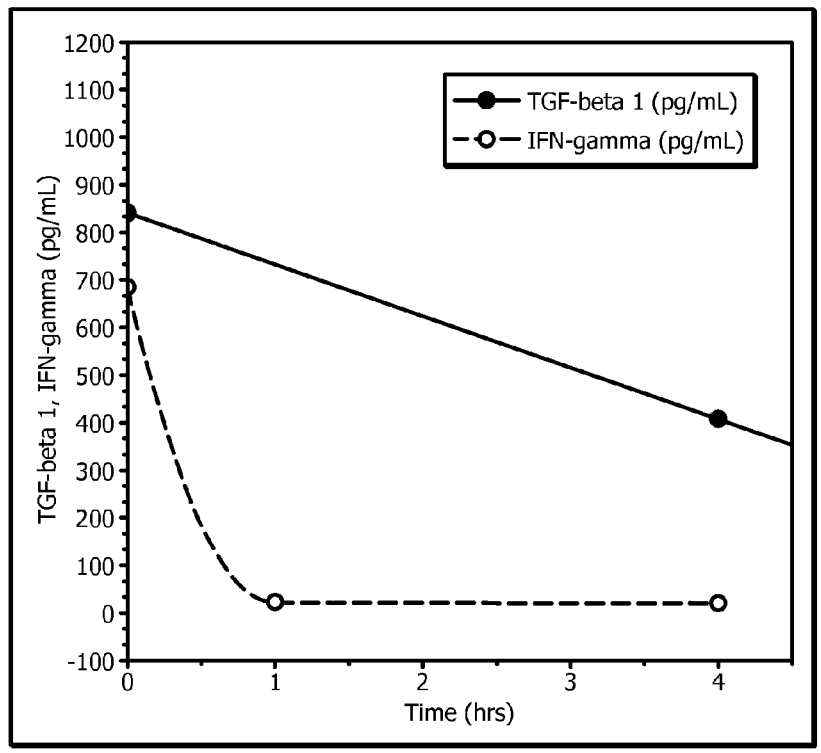
FIG. 5D is a plot of the amount of TGF-β and IFNγ in a sample of fresh frozen plasma as a function of time following contact with the indicated adsorbent.
Figure 5E:
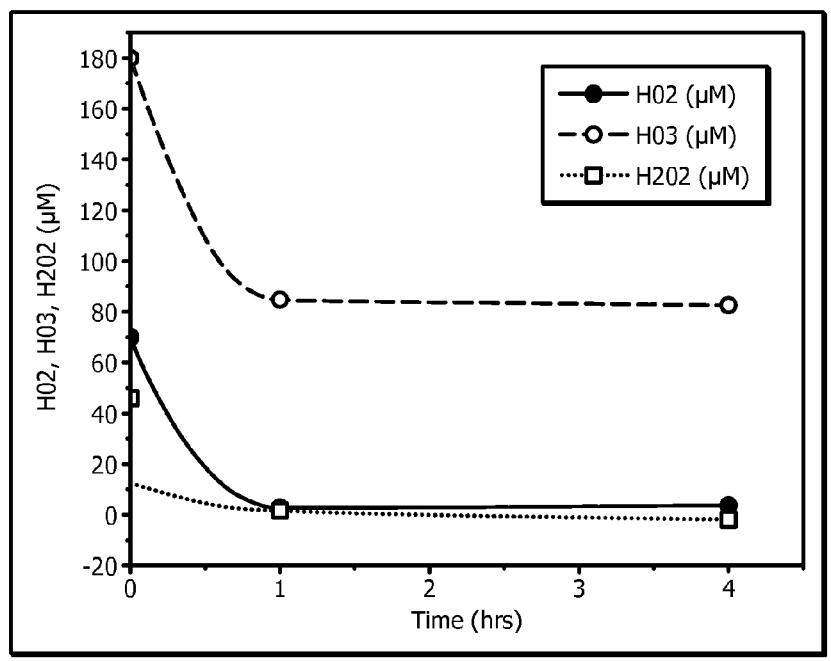
FIG. 5E is a plot of the amount of nitric oxide and hydrogen peroxide in a sample of fresh frozen plasma as a function of time following contact with the indicated adsorbent.
Figure 5F:
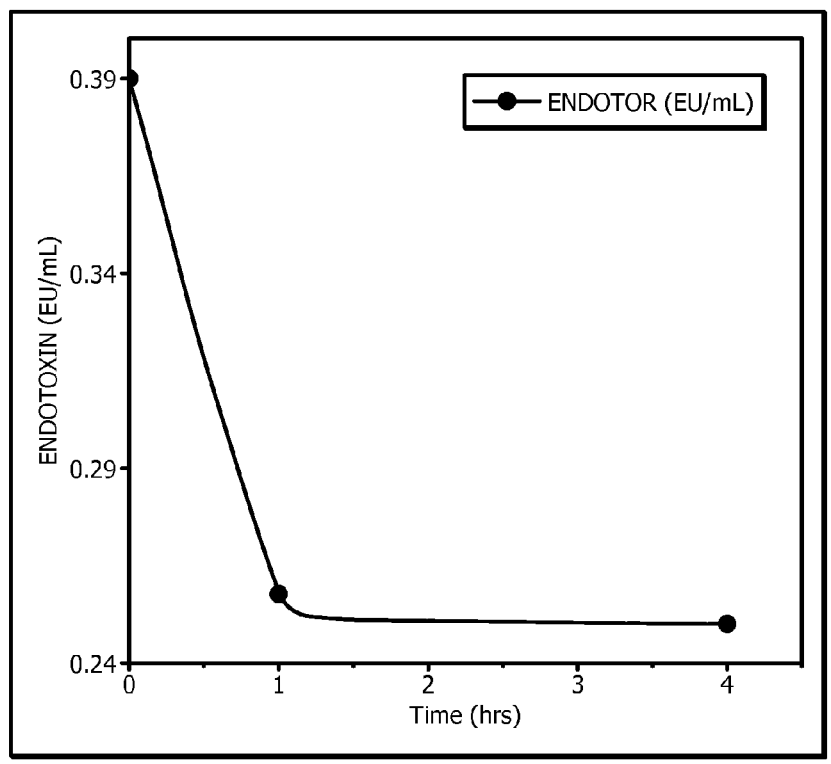
FIG. 5F is a plot of the amount of endotoxin in a sample of fresh frozen plasma as a function of time following contact with the indicated adsorbent.
Figure 6A:
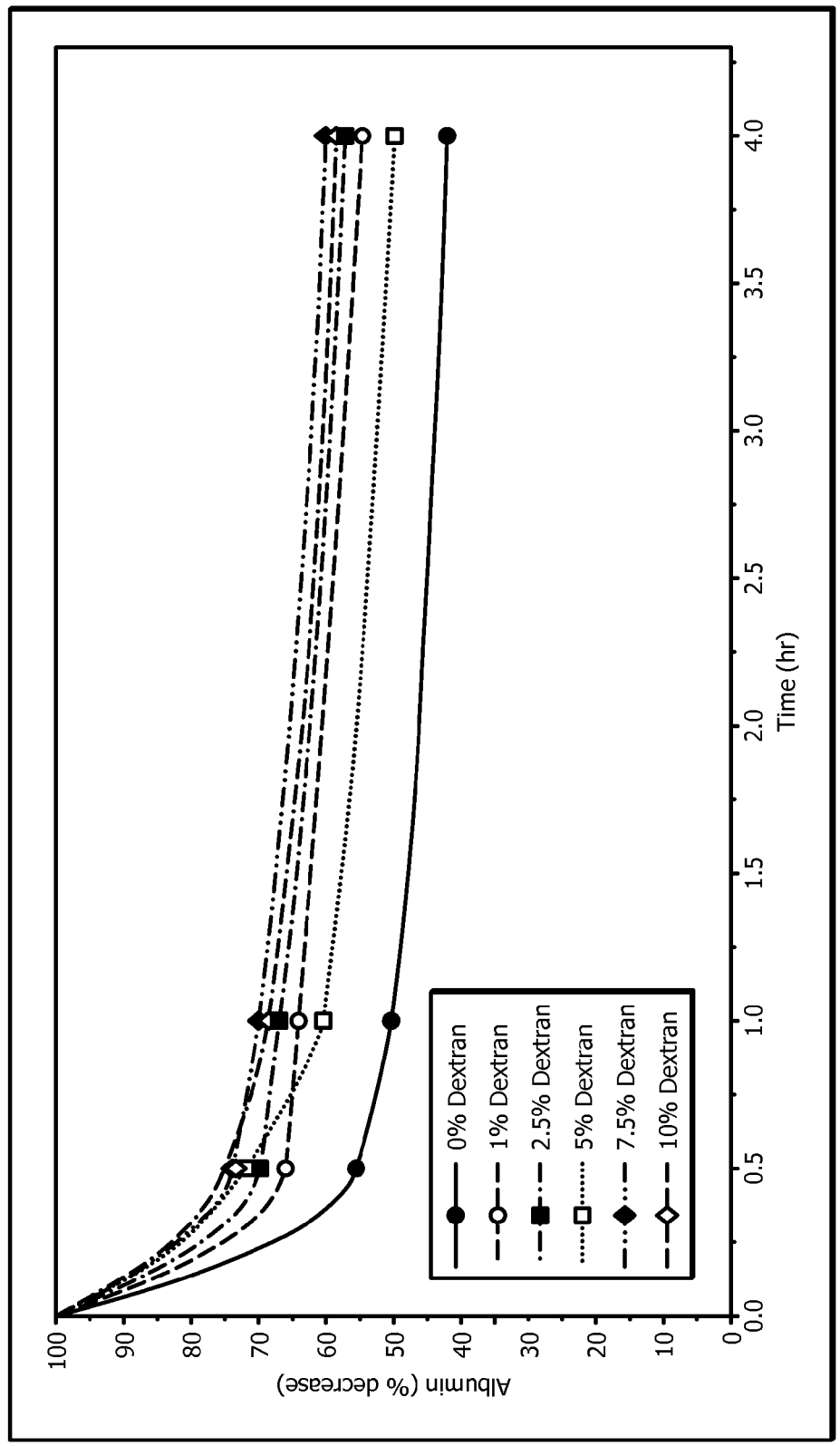
FIGS. 6A and 6B are plots of the amount of albumin in a sample of whole blood as a function of time following exposure to an adsorbent that had been primed with the indicated amount of dextran.
Figure 6B:
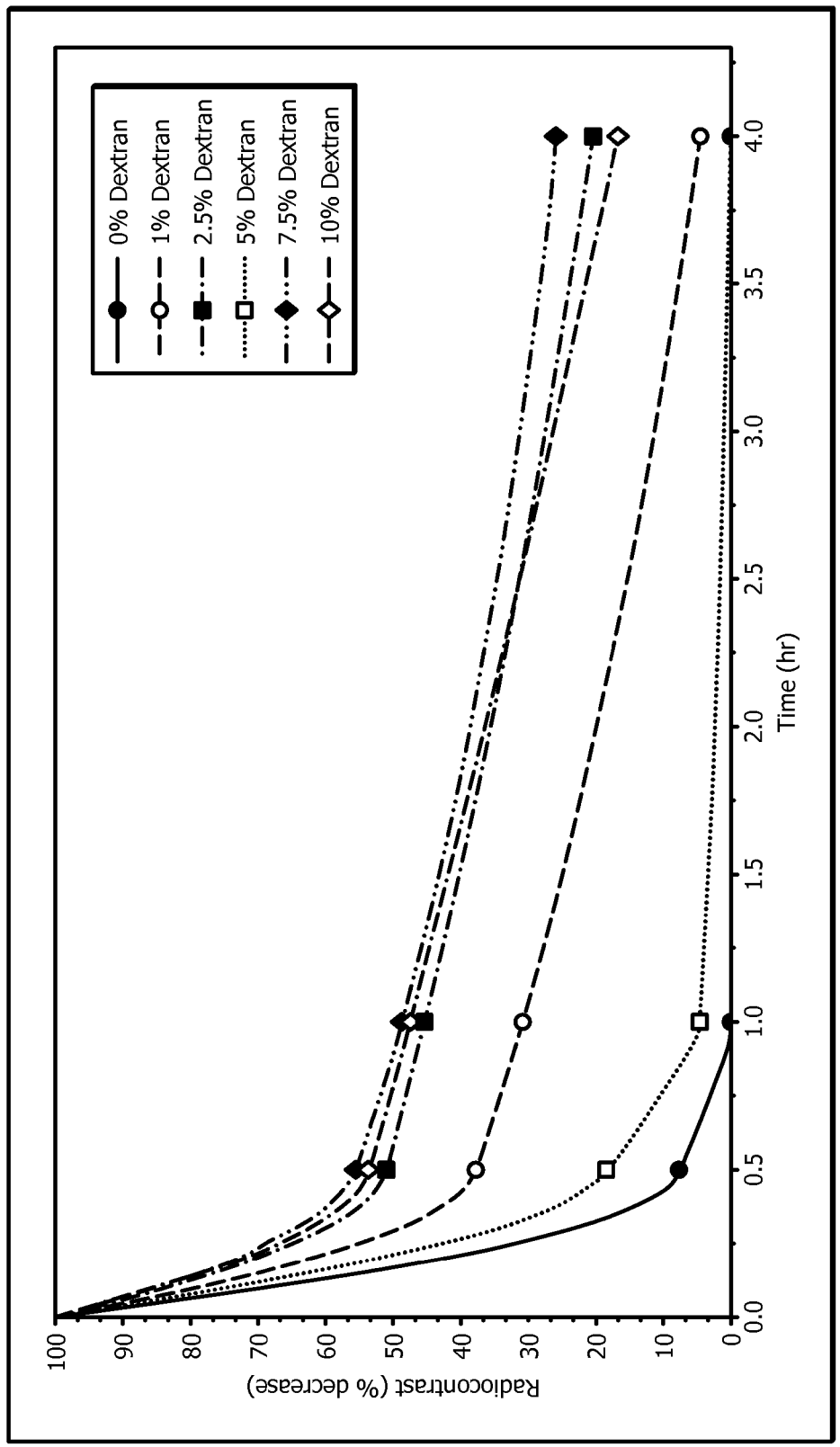

Mesoporous/micrporous synthetic carbon beads were primed/coated with dextran 40 in concentrations of: 0, 1, 2.5, 5, 7.5 and 10%, then utilized for extracorporeal removal of small molecules (radiocontrast Optiray 350) and large molecules (human albumin). The experiments were done as described in Example 4. Human albumin levels were established on Abaxis Piccolo Xpress Blood Chemistry Analyzer and radiocontrast with UV spectrophotometry. The results of coating mesoporous/microporous synthetic carbon beads with LMW dextran 40 on large molecule clearances (human albumin) are depicted in FIG. 4A while the results of coating mesoporous/microporous synthetic carbon beads with LMW dextran 40 on small molecule clearances (radiocontrast Optiray 350) is depicted in FIG. 4B.

The results demonstrate the observed sorbing modulation effect toward small and large molecules was time and concentration dependent. Dextran in higher concentrations (7.5-10%) obstructed the removal of both molecules. Dextran in lower concentrations (2.5-5%) showed a more enhanced removal, while 1% dextran had no effect. The results suggest dextran in highly concentrated form can be used as a method to restrict higher molecular weight compounds and permit sorption of small molecules. Without wishing to be limited by theory, the proposed mechanism of observed dextran-controlled sorbing activity can be explained by nonspecific incorporation of different numbers of 40 kDa dextran molecules into synthetic carbon pores, and their removal over time in exchange for target molecules. Besides, LMW dextran can serve as a lubricant during storage/shipment of devices containing synthetic carbon beads, by preventing formation of new fine particulates.

Example Seven

Animal Safety Study of Adsorbing Devices Containing Synthetic Carbon 250, Synthetic Carbon 125, Q Media and S Media.

This study, which received clearance from the TTUHSC IACUC (Protocol No. 13003), was designed to investigate the safety of the treatment with adsorption devices in a dog model. Experimental animals underwent a six-hour extracorporeal treatment with device containing 4 adsorbents: synthetic carbon 250, synthetic carbon 125, Q Media and S Media used in de-watered weight proportions: 50%. 20%. 20%, 10%, respectively. The adsorption devices were sterile, pyrogen free and highly hemo-biocompatible.

The animal study was designed to obtain information about clinical performance of the adsorption devices in healthy anesthetized dogs. This study determined the effect of the ImMutriX Adsorption Devices over 6 hours on: (i) hemodynamics; (ii) hematologic parameters; (iii) analytical blood chemistry parameters; and (iv) anatomo-histopathology. Data were collected at:—baseline after induction of anesthesia/catheter placement & prior to adsorption device treatment. Baseline laboratory consisted of: AST, ALT, LD, ALP, Albumin, Globulins, Ammonia, lactic acid, total protein, bilirubin, pH, $pO_2$, $pCO_2$, $Na^+$, $K^+$, $Cl^-$, $iCa^{++}$, tCa, $TCO_2$, $HCO_3$, BEb, BEecf, tCa, Mg, BUN and Creatinine, Glucose, complete blood count (Hg, Hct, RBC, WBC, differential, and platelets), coagulation panel: aPTT, PT, INR, D-Dimer and fibrinogen, hemodynamic monitoring (Vital signs Q15 min/Hemodynamics Q30 min), vital signs (blood pressure-M, S/D, oxygen saturation & temperature), hemodynamics (PAP, PCWP, CVP, CO, PVR & SVR), urinary output. During the treatment at: 30 min, 60 min, 120 min, 180 min, 240 min, 300 min, and 360 min (some parameters, including hemodynamics were also measured at 15 minutes, 90 min and 150 min), AST, ALT, LD, ALP, Albumin, Globulins, Ammonia, lactic acid, total protein, bilirubin, pH, $pO_2$, $pCO_2$, $Na^+$, $K^+$, $Cl^-$, $iCa^{++}$, tCa, $TCO_2$, $HCO_3$, BEb, BEecf, tCa, Mg, BUN and Creatinine, Glucose, complete blood count (Hg, Hct, RBC, WBC, differential, and platelets), coagulation panel: aPTT, PT, INR, D-Dimer and fibrinogen, hemodynamic monitoring (Vital signs Q15 min/Hemodynamics Q30 min), vital signs (blood pressure-M, S/D, oxygen saturation & temperature),hemodynamics (PAP, PCWP, CVP, CO, PVR & SVR), urinary output.

Necropsy and histopathological evaluation (H&E) of lung, liver, kidney, heart, and GI tract were also performed.

Tables 17-24 provide summaries of the data for the animal study. The recording of all hemodynamic parameters allowed a comprehensive evaluation of the hemodynamic effects of the adsorbing devices. A careful analysis of these parameters illustrates that the devices did not cause any significant changes in MAP, CVP, PCWP, PAP, SVR and PVR. Overall, the hemodynamic data leads to the conclusion that six hour extracorporeal treatment with the adsorbing devices was well tolerated by dogs.

TABLE 17

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| HR (b/min) | 98 | 96 | 93 | 93 | 92 | 90 | 90 | 89 | 90 | 87 | 89 | 90 | 77 | 82 |
| BP-SID (mmHg) | 94/52 | 110/54 | 110/58 | 118/65 | 115/60 | 105/53 | 103/53 | 105/46 | 105/53 | 109/53 | 95/48 | 102/43 | 107/53 | 118/58 |
| BP-M (mmHg) | 65 | 90 | 75 | 85 | 78 | 64 | 68 | 64 | 70 | 71 | 61 | 61 | 72 | 79 |
| CVP (mmHg) | 5 | 4 | 2 | 5 | 10 | 10 | 10 | 10 | 8 | 10 | 13 | 13 | 13 | 13 |
| PA-S/D (mmHg) | 34/18 | 27/8 | 24/8 | 22/7 | 30/18 | 24/14 | 24/14 | 29/17 | 24/14 | 29/18 | 25/16 | 31/20 | 32/22 | 28/18 |
| PA-M (mmHg) | 23.3 | 14.3 | 13.3 | 12 | 22 | 17.3 | 17.3 | 21 | 17.3 | 21.7 | 19 | 23.7 | 25.3 | 21.3 |
| PCWP (mmHg) | Not recorded | For PVR: arbitrary: 10 | — | — | — | — | — | — | — | — | — | — | — | — |
| CO (L/min) | 4.1 | 5.8 | 4.1 | 4.0 | 4.0 | 3.9 | 4.3 | 4.3 | 3.8 | 3.9 | 3.7 | 3.9 | 4.5 | 4.0 |
| PVR (dyne s cm$^{-5}$) | 259 | 59.3 | 64.4 | 40 | 240 | 149.7 | 135.8 | 204.6 | 153.7 | 240 | 194.6 | 266.7 | 272 | 226 |
| SVR (dyne s cm$^{-5}$) | 1169 | 1171 | 1364 | 1598 | 1358 | 1106 | 1077 | 1096 | 1303 | 1250 | 1144 | 983 | 1047 | 1318 |
| Urine Output (mL) | 60 | 0 | 20 | 15 | 23 | 10 | 15 | 10 | 15 | 17 | 7 | 23 | 10 | 34 |

TABLE 18

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| pH (U) | 7.405 | 7.306 | 7.322 | 7.318 | — | 7.352 | — | 7.405 | — | 7.392 | — | 7.372 | — | 7.380 |
| pCO2 (mmHg) | 31.3 | 39.2 | 47.7 | 47.0 | — | 40.1 | — | 37.0 | — | 41.2 | — | 42.8 | — | 42.9 |
| pO2 (mmHg) | 321.6 | 309.9 | 380.0 | 353.6 | — | 318.9 | — | 168.8 | — | 371.8 | — | 381.7 | — | 388.5 |
| Na+ (mM) | 148.8 | 149.4 | 150.2 | 150.7 | — | 150.4 | — | 147.0 | — | 147.2 | — | 146.7 | — | 146.6 |
| K+ (mM) | 2.93 | 2.68 | 2.84 | 2.78 | — | 2.69 | — | 3.44 | — | 3.20 | — | 3.02 | — | 2.92 |
| iCa++ (mM) | 1.47 | 1.16 | 1.27 | 1.31 | — | 1.22 | — | 1.23 | — | 1.33 | — | 1.36 | — | 1.30 |
| HCO3- (mM) | 19.4 | 19.4 | 24.4 | 23.8 | — | 22.0 | — | 22.9 | — | 24.7 | — | 24.6 | — | 25.1 |
| TCO2 (mM) | 20.3 | 20.6 | 25.9 | 25.3 | — | 23.2 | — | 24.0 | — | 26.0 | — | 25.9 | — | 26.4 |
| BEb (mM) | -3.6 | -5.8 | -1.5 | -2.0 | — | -2.7 | — | -0.8 | — | 0.4 | — | -0.2 | — | 0.4 |

TABLE 18-continued

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| BEecf (mM) | −5.6 | −7.2 | −1.9 | −2.5 | — | −3.8 | — | −2.0 | — | −0.4 | — | −0.9 | — | −0.3 |
| O2Sat (%) | 99.7 | 99.7 | 99.8 | 99.7 | — | 99.7 | — | 99.1 | — | 99.8 | — | 99.8 | — | 99.8 |

TABLE 19

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| THb (g/dL) | 9.8 | — | 12.1 | 12.0 | — | 9.8 | — | 10.3 | — | 9.9 | — | 10.4 | — | 8.9 |
| OxyHb (%) | 90.4 | — | 90.2 | 90.4 | — | 90.9 | — | 89.9 | — | 90.4 | — | 90.5 | — | 89.6 |
| COHb (%) | 9.9 | — | 10.0 | 9.8 | — | 10.1 | — | 9.1 | — | 9.7 | — | 10.0 | — | 9.7 |
| MetHb (%) | 0.5 | — | 0.5 | 0.5 | — | −0.3 | — | 0.9 | — | 0.5 | — | 0.4 | — | 0.9 |
| RHb (Reduced Hb-%) | −0.7 | — | −0.7 | −0.7 | — | −0.7 | — | 0.1 | — | −0.6 | — | −0.9 | — | −0.2 |
| O2 Content (mL/dL) | 12.3 | — | 15.2 | 15.0 | — | 12.4 | — | 12.9 | — | 12.4 | — | 13.1 | — | 11.1 |
| O2 Capacity (mL/dL) | 12.2 | — | 15.1 | 15.0 | — | 12.3 | — | 12.9 | — | 12.4 | — | 13.0 | — | 11.1 |

TABLE 20

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| Sodium mmol/L (128-145) | 141 | — | 137 | 137 | — | 136 | — | 138 | — | 136 | — | 135 | — | 137 |
| Potassium mmol/L (3.6-5.1) | 3.0 | — | 2.9 | 3.0 | — | 2.9 | — | 3.4 | — | 3.3 | — | 3.1 | — | 3.2 |
| Chloride mmol/L (90-108) | 110 | — | 111 | 112 | — | 114 | — | 111 | — | 112 | — | 110 | — | 109 |
| Total CO2 mmol/L (18-33) | 20 | — | 25 | 25 | — | 23 | — | 26 | — | 26 | — | 26 | — | 27 |
| Creatinine mg/dL (0.6-1.2) | 0.6 | — | 0.6 | 0.7 | — | 0.4 | — | 0.3 | — | 0.5 | — | 0.2 | — | 0.4 |
| BUN mg/dL (7-22) | 14 | — | 14 | 14 | — | 12 | — | 11 | — | 12 | — | 11 | — | 11 |
| Glucose mg/dL (73-118) | 150 | — | 156 | 166 | — | 146 | — | 168 | — | 167 | — | 175 | — | 164 |
| Total Calcium mg/dL (8.0-10.3) | 10.2 | — | 7.5 | 8.2 | — | 7.1 | — | 7.8 | — | 8.1 | — | 8.0 | — | 8.1 |
| Magnesium mg/dL (1.6-2.3) | 1.6 | — | 1.4 | 1.5 | — | 1.3 | — | 1.6 | — | 1.6 | — | 1.6 | — | 1.7 |

TABLE 20-continued

| | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| Lactate Dehydrogenase U/L (99-192) | 195 | — | 96 | 128 | — | 97 | — | 69 | — | 54 | | 73 | | 76 |

TABLE 21

| | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| Albumin g/dL (2.5-4.4) | 1.6 | — | 1.6 | 1.6 | — | 1.2 | 1.2 | 1.2 | — | 1.3 | — | 1.4 | — | 1.3 |
| ALP U/L (20-150) | 35 | — | 36 | 36 | — | 39 | 39 | 40 | — | 48 | — | 46 | — | 53 |
| ALT U/L (10-118) | 12 | — | 14 | 10 | — | 11 | 11 | 13 | — | 14 | — | 15 | — | 14 |
| Amylase U/L (200-1200) | 367 | — | 381 | 393 | — | 338 | 334 | 369 | — | 401 | — | 417 | — | 402 |
| Total Bilirubin mg/dL (0.1-0.6) | 0.3 | — | 0.3 | 0.3 | — | 0.2 | 0.3 | 0.3 | — | 0.3 | — | 0.3 | — | 0.3 |
| BUN mg/dL (7-25) | 13 | — | 14 | 13 | — | 11 | 11 | 12 | — | 12 | — | 11 | — | 10 |
| Total Calcium mg/dL (8.6-11.8) | 7.1 | — | 7.9 | 8.0 | — | 6.9 | 7.0 | 7.3 | — | 8.0 | — | 7.9 | — | 7.8 |
| Phosphorus mg/dL (2.9-6.6) | 5.2 | — | 6.4 | 6.1 | — | 5.2 | 5.7 | 6.0 | — | 5.7 | — | 5.3 | — | 5.1 |
| Creatinine mg/dL (0.3-1.4) | 1.0 | — | 0.9 | 1.2 | — | 0.7 | 0.6 | 0.4 | — | 0.6 | — | 0.5 | — | 0.5 |
| Glucose mg/dL (60-110) | 135 | — | 151 | 161 | — | 144 | 142 | 165 | — | 165 | — | 172 | — | 163 |
| Sodium mmol/L (138-160) | 139 | — | 139 | 139 | — | 139 | 139 | 138 | — | 138 | — | 138 | — | 139 |
| Potassium mmol/L (3.7-5.8) | 2.3 | — | 2.5 | 2.5 | — | 2.3 | 2.2 | 3.2 | — | 3.0 | — | 3.0 | — | 2.6 |
| Total Protein g/dL (5.4-8.2) | 3.1 | — | 3.1 | 3.1 | — | 2.6 | 2.6 | 2.7 | — | 2.7 | — | 2.7 | — | 2.7 |
| Globulin g/dL (2.3-5.2) | 1.5 | — | 1.5 | 1.5 | — | — | 1.5 | 1.5 | — | 1.5 | — | 0.0 | — | 0.0 |

TABLE 22

| | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| PT sec (9.3-12.1) | 8.4 | — | 9.8 | 9.4 | — | 11.9 | — | 13.7 | — | 13.1 | — | 12.7 | — | 15.0 |

TABLE 22-continued

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| International Normalized Ratio (INR) | 0.75 | — | 0.88 | 0.84 | — | 1.07 | — | 1.24 | — | 1.19 | — | 1.15 | — | 1.36 |
| PTT sec (26.1-37.9) | 178.0 | >400 | 216.4 | 101.7 | >400 | 217.0 | 237.6 | 187.3 | 145.6 | 197.4 | 156.6 | >400 | 311.0 | 211.5 |
| Fibrinogen mg/dL (197-406) | 56.0 | — | 78.0 | 57.0 | — | 54.0 | — | 51.0 | — | 56.0 | — | 55.0 | — | 52.0 |
| D-Dimer ng/mL (0-243) | 165 | — | <150 | <150 | — | <150 | — | <150 | — | <150 | — | <150 | — | <150 |

TABLE 23

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| Lactic Acid mmol/L (0.5-2.2) | 3.2 | — | 2.5 | 2.5 | — | 1.3 | — | 1.1 | — | — | — | 1.1 | — | 1.3 |
| Ammonia mcmol/L (56-92) | 21 | — | 24 | 27 | — | 11 | — | 14 | — | — | — | 13 | — | 27 |

TABLE 24

|  | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| WBC ($10^9$/L) | 3.14 | — | 3.75 | 4.22 | — | 4.04 | — | 4.97 | — | 5.88 | — | 5.82 | — | 6.04 |
| LYMPH ($10^9$/L) | 0.89 | — | 0.90 | 1.22 | — | 0.87 | — | 0.92 | — | 1.29 | — | 1.02 | — | 1.46 |
| MONO ($10^9$/L) | 0.18 | — | 0.15 | 0.22 | — | 0.26 | — | 0.27 | — | 0.46 | — | 0.41 | — | 0.42 |
| NEUT ($10^9$/L) | 2.06 | — | 2.69 | 2.79 | — | 2.91 | — | 3.78 | — | 4.13 | — | 4.39 | — | 4.16 |
| EOS ($10^9$/L) | 0.01 | — | 0.01 | 0.00 | — | 0.00 | — | 0.00 | — | 0.00 | — | 0.00 | — | 0.00 |
| BASO ($10^9$/L) | 0.00 | — | 0.00 | 0.00 | — | 0.00 | — | 0.00 | — | 0.00 | — | 0.00 | — | 0.00 |
| LYMPH (%) | 28.3 | — | 24.0 | 28.8 | — | 21.6 | — | 18.4 | — | 22.0 | — | 17.5 | — | 24.2 |
| MONO (%) | 5.7 | — | 4.0 | 5.1 | — | 6.4 | — | 5.4 | — | 7.8 | — | 7.0 | — | 6.9 |
| NEUT (%) | 65.8 | — | 71.8 | 66.0 | — | 72.0 | — | 76.1 | — | 70.2 | — | 75.4 | — | 69.8 |
| EOS (%) | 0.2 | — | 0.1 | 0.1 | — | 0.1 | — | 0.0 | — | 0.0 | — | 0.0 | — | 0.1 |
| BASO (%) | 0.0 | — | 0.0 | 0.0 | — | 0.0 | — | 0.0 | — | 0.0 | — | 0.0 | — | 0.0 |
| RBC ($10^{12}$/L) | 4.12 | — | 4.89 | 4.92 | — | 4.06 | — | 4.17 | — | 3.96 | — | 4.29 | — | 3.63 |
| Hb (g/dL) | 9.7 | — | 11.9 | 11.6 | — | 9.5 | — | 9.8 | — | 9.6 | — | 10.3 | — | 8.5 |
| HCT (%) | 28.17 | — | 33.58 | 34.04 | — | 28.13 | — | 28.65 | — | 26.97 | — | 29.73 | — | 24.84 |

TABLE 24-continued

| | Baseline (3-1) | 15 (3-1-1) | 30 (3-2) | 60 (3-3) | 90 (3-3-1) | 120 (3-4) | 150 (3-4-1) | 180 (3-5) | 210 (3-5-1) | 240 (3-6) | 270 (3-6-1) | 300 (3-7) | 330 (3-7-1) | 360 (3-8) |
|---|---|---|---|---|---|---|---|---|---|---|---|---|---|---|
| MCV (u) | 68 | — | 69 | 69 | — | 69 | — | 69 | — | 68 | — | 69 | — | 68 |
| MCH (pg) | 23.4 | — | 24.3 | 23.5 | — | 23.3 | — | 23.5 | — | 24.3 | — | 24.1 | — | 23.5 |
| MCHC (g/dL) | 34.3 | — | 35.4 | 33.9 | — | 33.7 | — | 34.2 | — | 35.6 | — | 34.8 | — | 34.3 |
| RDWc (%) | 14.8 | — | 15.0 | 15.2 | — | 14.6 | — | 15.0 | — | 14.6 | — | 14.8 | — | 15.0 |
| PLT (10^9/L) | 113 | — | 152 | 149 | — | 116 | — | 127 | — | 121 | — | 120 | — | 102 |
| PCT (%) | 0.12 | — | 0.17 | 0.16 | — | 0.13 | — | 0.13 | — | 0.13 | — | 0.14 | — | 0.11 |
| MPV (u) | 10.3 | — | 11.0 | 10.7 | — | 11.1 | — | 10.5 | — | 11.1 | — | 11.4 | — | 10.8 |
| PDWc (%) | 36.9 | — | 39.0 | 39.2 | — | 38.9 | — | 38.6 | — | 38.5 | — | 39.8 | — | 38.8 |

The following are enumerated embodiments are provided as non-limiting examples:

A first embodiment which is a method comprising obtaining a bodily fluid from a subject having a level of disease mediators (y); contacting the bodily fluid with an adsorbent material comprising an synthetic carbon particle (SCP) to produce a first filtrate; contacting the first filtrate with an adsorbent material comprising the SCP and an anion exchange resin where the weight ratio of SCP to anion exchange resin is from about 0.1:100 to 100:0.1 to produce a second filtrate; contacting the second filtrate with an adsorbent material comprising the SCP and a cation exchange resin where the weight ratio of SCP to cation exchange resin is from about 0.1:100 to 100:0.1 produce a third filtrate; and administering the third filtrate to the subject.

A second embodiment which is the method of the first embodiment wherein the subject is diagnosed with or suspected of having viruses associated with immunosuppressive events.

A third embodiment which is the method of any of the first through second embodiments wherein the viruses associated with immunosuppressive events is a member of a viral family selected from the group consisting of Arenaviridae, Bunyaviridae, Filoviridae, Flaviviridae, Coronavirinae, Bunyaviridae, and Orthomyxoviridae.

A fourth embodiment which is the method of any of the second through third embodiments wherein the virus comprises Hantavirus, MERS-coronavirus (MERS-CoV), Influenza A virus subtype H5N1, Influenza A (H1N1) virus, Ebola Virus, Marburg virus, or combinations thereof.

A fifth embodiment which is the method of any of the first through fourth embodiments further comprising sanitizing the SCP, the anion exchange resin, and the cation exchange resin prior to contacting with the bodily fluids.

A sixth embodiment which is the method of any of the first through fifth embodiments comprising contacting the SCP, the anion exchange resin, and the cation exchange resin with a compatibilizer prior to contacting the SCP, the anion exchange resin, and the cation exchange resin with the bodily fluids.

A seventh embodiment which is the method of the sixth embodiment wherein the compatibilizer comprises a polysaccharide, a glucan, albumin, mannitol, a starch, or combinations thereof.

An eighth embodiment which is the method of any of the sixth through seventh embodiments wherein the compatibilizer comprises dextran.

A ninth embodiment which is the method of the seventh embodiment wherein the dextran has an average molecular weight of from about 1 kDa to about 500 kDa.

A tenth embodiment which is the method of the seventh embodiment wherein the compatibilizer comprises hydroxyethyl starch.

An eleventh embodiment which is the method of the seventh embodiment wherein the compatibilizer comprises albumin and mannitol.

A twelfth embodiment which is the method of any of the first through eleventh embodiments wherein a level of a disease mediator in the third filtrate is reduced by about 100% when compared to the level of disease mediators (y).

A thirteenth embodiment which is the method of the twelfth embodiment wherein the disease mediators are selected from the group consisting of IL-18, IFN-γ, TNF-α, IL-1β, IL-6, IL-10, MCP-1, MCSF, MIP-1α, NO, C3a, C5a, histamine, and combinations thereof.

A fourteenth embodiment which is an extracorporeal system comprising at least three adsorbent materials, an access disconnection detector, and a computer system.

A fifteenth embodiment which is the extracorporeal system of the fourteenth embodiment wherein the adsorbent materials comprise an synthetic carbon particle, a mixture of an synthetic carbon particle and an anion exchange resin, and a mixture of a synthetic carbon particles (SCP) and a cation exchange resin.

A sixteenth embodiment which is the extracorporeal system of the fourteenth through fifteenth embodiments wherein the SCP and the anion exchange resin are present in a ratio of 1 wt. % SCP to 99 wt. % anion exchange resin.

A seventeenth embodiment which is the extracorporeal system of any of the fourteenth through sixteenth embodiments wherein the SCP and the cation exchange resin are present in a ratio of 1 wt. % SCP to 99 wt. % cation exchange resin.

An eighteenth embodiment which is the extracorporeal system of any of the fourteenth through seventeenth embodiments wherein the at least three adsorbent materials have at least a portion of their surface coated with a compatibilizer.

A nineteenth embodiment which is the extracorporeal system of the eighteenth embodiment wherein the compatibilizer comprises a glucan.

A twentieth embodiment which is the extracorporeal system of any of the eighteenth through nineteenth embodiments wherein the compatibilizer comprises dextran.

A twenty-first embodiment which is the extracorporeal system of FIG. 1.

While embodiments of the present disclosure have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Background is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

Unless indicated otherwise, when a range of any type is disclosed or claimed it is intended to disclose or claim individually each possible number that such a range could reasonably encompass, including any sub-ranges encompassed therein. When describing a range of measurements every possible number that such a range could reasonably encompass can, for example, refer to values within the range with one significant digit more than is present in the end points of a range. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure.

What is claimed is:

1. A method comprising:
    obtaining a bodily fluid from a subject having a level of disease mediators (y);
    contacting the bodily fluid with an adsorbent material comprising a synthetic carbon particle (SCP) to produce a first filtrate, wherein the SCP consists essentially of pores with diameters larger than 50 nm;
    contacting the first filtrate with an adsorbent material comprising the SCP and an anion exchange resin where the weight ratio of SCP to anion exchange resin is from about 1:100 to produce a second filtrate;
    contacting the second filtrate with an adsorbent material comprising the SCP and a cation exchange resin where the weight ratio of SCP to cation exchange resin is from about 1:100 to produce a third filtrate; and
    administering the third filtrate to the subject.

2. The method of claim 1 wherein the subject is diagnosed with or suspected of having viruses associated with immunosuppressive events.

3. The method of claim 2 wherein the viruses associated with immunosuppressive events is a member of a viral family selected from the group consisting of Arenaviridae, Bunyaviridae, Filoviridae, Flaviviridae, Coronavirinae, Bunyaviridae, and Orthomyxoviridae.

4. The method of claim 2 wherein the virus comprises Hantavirus, MERS-coronavirus (MERS-CoV), Influenza A virus subtype H5N1, Influenza A (H1N1) virus, Ebola Virus, Marburg virus, or combinations thereof.

5. The method of claim 1 further comprising contacting the SCP, the anion exchange resin, and the cation exchange resin with a compatibilizer prior to contacting the SCP, the anion exchange resin, and the cation exchange resin with the bodily fluids.

6. The method of claim 5 wherein the compatibilizer comprises a polysaccharide, a glucan, albumin, mannitol, a starch, or combinations thereof.

7. The method of claim 5 wherein the compatibilizer comprises dextran.

8. The method of claim 7 wherein the dextran has an average molecular weight of from about 1 kDa to about 500 kDa.

9. The method of claim 5 wherein the compatibilizer comprises hydroxyethyl starch.

10. The method of claim 5 wherein the compatibilizer comprises albumin and mannitol.

11. The method of claim 1 wherein a level of a disease mediator in the third filtrate is reduced by about 100% when compared to the level of disease mediators (y).

12. The method of claim 11 wherein the disease mediators are selected from the group consisting of IL-18, IFN-γ, TNF-α, IL-1β, IL-6, IL-10, MCP-1, MCSF, MIP-1α, NO, C3a, C5a, histamine, and combinations thereof.

13. The method of claim 1 wherein the adsorbent material has a bioburden maximum of 20 endotoxins units.

14. The method of claim 1 wherein the SCP comprises a mixture of carbon particle populations, a first population having macroporous size a and a second population having macroporous size β and wherein the pore size of the first population is approximately twice the pore size of the second population.

15. The method of claim 1 further comprising sanitizing the SCP, the anion exchange resin, and the cation exchange resin prior to contacting with bodily fluids.

16. The method of claim 1 wherein the SCP comprises a trimodal pore size distribution wherein the pore size of a first population is approximately twice the pore size of a second population and a pore size of a third population is approximately two and a half times the pore size of the second population.

* * * * *